(12) United States Patent
Takada

(10) Patent No.: US 11,832,512 B2
(45) Date of Patent: Nov. 28, 2023

(54) ORGANIC ELECTROLUMINESCENCE DEVICE AND MONOAMINE COMPOUND FOR ORGANIC ELECTROLUMINESCENCE DEVICE

(71) Applicant: Samsung Display Co., Ltd., Yongin-si (KR)

(72) Inventor: Ichinori Takada, Tsurumi-ku (JP)

(73) Assignee: Samsung Display Co., Ltd., Yongin-si (KR)

( * ) Notice: Subject to any disclaimer, the term of this patent is extended or adjusted under 35 U.S.C. 154(b) by 783 days.

(21) Appl. No.: 16/565,332

(22) Filed: Sep. 9, 2019

(65) Prior Publication Data

US 2020/0168797 A1    May 28, 2020

(30) Foreign Application Priority Data

Nov. 23, 2018    (KR) .................. 10-2018-0146635

(51) Int. Cl.
| | | |
|---|---|---|
| C07D 307/91 | (2006.01) | |
| H10K 85/60 | (2023.01) | |
| C07C 211/54 | (2006.01) | |
| H10K 50/15 | (2023.01) | |
| H10K 50/17 | (2023.01) | |
| H10K 71/00 | (2023.01) | |
| H10K 71/16 | (2023.01) | |
| H10K 102/00 | (2023.01) | |

(52) U.S. Cl.
CPC .......... H10K 85/633 (2023.02); C07C 211/54 (2013.01); C07D 307/91 (2013.01); H10K 85/636 (2023.02); H10K 50/15 (2023.02); H10K 50/17 (2023.02); H10K 71/00 (2023.02); H10K 71/164 (2023.02); H10K 85/6574 (2023.02); H10K 2102/351 (2023.02)

(58) Field of Classification Search
None
See application file for complete search history.

(56) References Cited

U.S. PATENT DOCUMENTS

| | | |
|---|---|---|
| 8,304,095 B2 | 11/2012 | Heil et al. |
| 9,065,060 B2 | 6/2015 | Hong et al. |
| 9,799,833 B2 | 10/2017 | Mujica-Fernaud et al. |
| 9,960,360 B2 | 5/2018 | Kawamura et al. |
| 10,923,663 B2 | 2/2021 | Takada et al. |

(Continued)

FOREIGN PATENT DOCUMENTS

| | | |
|---|---|---|
| CN | 103403125 A | 11/2013 |
| CN | 107973722 A | 5/2018 |
| JP | 3915256 B2 | 5/2007 |

(Continued)

OTHER PUBLICATIONS

KR20090104573 translated from epo website Apr. 9, 2022 pp. 1-48.*

(Continued)

*Primary Examiner* — Alexander R Pagano

(74) *Attorney, Agent, or Firm* — Lewis Roca Rothgerber Christie LLP

(57) ABSTRACT

An organic electroluminescence device including a monoamine compound represented by the following Formula 1 in at least one of a plurality of organic layers, and a monoamine compound represented by the following Formula 1 are provided. The monoamine compound represented by Formula 1 may be represented by the following Formula 2-1 or 2-2.

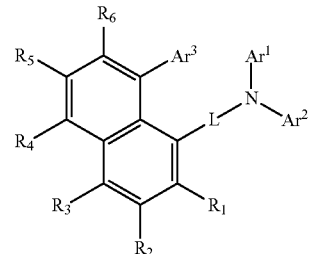

Formula 1

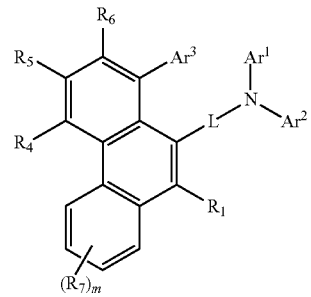

Formula 2-1

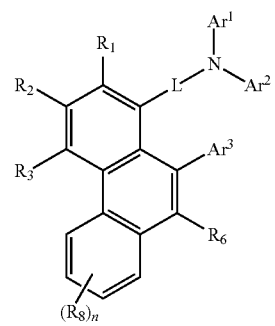

Formula 2-2

20 Claims, 2 Drawing Sheets

(56) References Cited

U.S. PATENT DOCUMENTS 11,575,087 B1 * 2/2023 Toyoshima ............ H10K 85/40
2017/0018710 A1 1/2017 Mujica-Fernaud et al.

FOREIGN PATENT DOCUMENTS

| | | | | |
|---|---|---|---|---|
| JP | 5616582 | B2 | 10/2014 | |
| JP | 2017-513815 | A | 6/2017 | |
| JP | 6324950 | B2 | 5/2018 | |
| KR | 20090104573 | * | 9/2009 | ............ H01L 51/00 |
| KR | 10-1233379 | B1 | 2/2013 | |
| KR | 10-2013-0121597 | A | 11/2013 | |
| KR | 10-1352300 | B1 | 1/2014 | |
| KR | 10-1422864 | B1 | 7/2014 | |
| KR | 10-2015-0023657 | A | 3/2015 | |
| KR | 10-1756611 | B1 | 7/2017 | |
| KR | 10-1854886 | B1 | 5/2018 | |
| KR | 10-1868505 | B1 | 6/2018 | |
| WO | WO 2012/099376 | A2 | 7/2012 | |
| WO | WO 2015/131976 | A1 | 9/2015 | |

OTHER PUBLICATIONS

KR20090104573 translation page, 2022, this page is provided to show the case number in the web address header because the foreign document and translation do not show KR20090104573 anywhere in the document.*

WO2012099376 machine translation from Google patents downloaded Oct. 22, 2022.*

* cited by examiner

ORGANIC ELECTROLUMINESCENCE DEVICE AND MONOAMINE COMPOUND FOR ORGANIC ELECTROLUMINESCENCE DEVICE

CROSS-REFERENCE TO RELATED APPLICATION

This application claims priority to and the benefit of Korean Patent Application No. 10-2018-0146635, filed on Nov. 23, 2018, in the Korean Intellectual Property Office (KIPO), the entire content of which is hereby incorporated by reference.

BACKGROUND

1. Field

Embodiments of the present disclosure relate to a monoamine compound and an organic electroluminescence device including the same.

2. Description of the Related Art

Development on an organic electroluminescence display as an image display is being actively conducted. An organic electroluminescence display is different from a liquid crystal display, and is a so-called self-luminescent display which accomplishes display (e.g., showing of an image) by recombining holes and electrons injected from a first electrode and a second electrode in an emission layer, and emitting light from a luminescent material (which is an organic compound) included in the emission layer.

As an organic electroluminescence device, for example, an organic electroluminescence device composed of a first electrode, a hole transport layer disposed on the first electrode, an emission layer disposed on the hole transport layer, an electron transport layer disposed on the emission layer, and a second electrode disposed on the electron transport layer is generally available in the art. Holes are injected from the first electrode, and the injected holes move via the hole transport layer to be injected into the emission layer. Also, electrons are injected from the second electrode, and the injected electrons move via the electron transport layer to be injected into the emission layer. By recombining the holes and electrons injected into the emission layer, excitons are generated in the emission layer. The organic electroluminescence device emits light during the transition of the excitons back to a ground state.

In an application of an organic electroluminescence device to a display, the increase of emission efficiency and extension of life (e.g., lifespan) for the organic electroluminescence device are desired, and development of materials which may reliably implement the desired features in the organic electroluminescence device is being continuously researched.

SUMMARY

Aspects of embodiments of the present disclosure are directed toward an organic electroluminescence device and a monoamine compound utilized for the same.

According to an embodiment of the present disclosure, an organic electroluminescence device includes a first electrode, a second electrode on the first electrode, and a plurality of organic layers between the first electrode and the second electrode, in which at least one of the plurality of organic layers may include a monoamine compound represented by the following Formula 1.

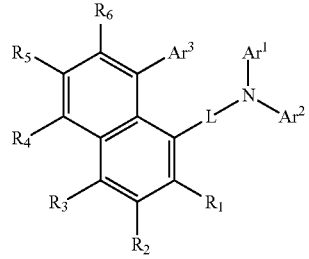

Formula 1

In Formula 1, L may be a direct linkage, a substituted or unsubstituted arylene group having 6 to 30 carbon atoms for forming a ring, or a substituted or unsubstituted heteroarylene group having 2 to 30 carbon atoms for forming a ring. $Ar_1$ and $Ar_2$ may be each independently a substituted or unsubstituted aryl group having 6 to 30 carbon atoms for forming a ring, or a substituted or unsubstituted heteroaryl group having 2 to 30 carbon atoms for forming a ring. $Ar_3$ may be a substituted or unsubstituted aryl group having 6 to 30 carbon atoms for forming a ring, or a substituted or unsubstituted heteroaryl group having 2 to 30 carbon atoms for forming a ring. $R_1$ to $R_6$ may be each independently a hydrogen atom, a deuterium atom, a halogen atom, a cyano group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted alkoxy group having 1 to 20 carbon atoms, a substituted or unsubstituted alkylthio group having 1 to 20 carbon atoms, or a substituted or unsubstituted silyl group having 1 to 40 carbon atoms, and one pair of $R_2$ and $R_3$, or $R_4$ and $R_5$ may combine with each other to form a substituted or unsubstituted benzene ring.

In an embodiment, L may be a substituted or unsubstituted phenylene group, a substituted or unsubstituted divalent biphenyl group, or a substituted or unsubstituted dibenzofuranylene group.

In an embodiment, $Ar_1$ and $Ar_2$ may be each independently a substituted or unsubstituted phenyl group, a substituted or unsubstituted biphenyl group, a substituted or unsubstituted fluorenyl group, a substituted or unsubstituted dibenzofuranyl group, or a substituted or unsubstituted dibenzothiophenyl group.

In an embodiment, $Ar_1$ and $Ar_2$ may be each independently an aryl group having 6 to 30 carbon atoms for forming a ring substituted with a phenyl group or a naphthyl group.

In an embodiment, $Ar_3$ may be a substituted or unsubstituted phenyl group, a substituted or unsubstituted biphenyl group, or a substituted or unsubstituted naphthyl group.

In an embodiment, the monoamine compound represented by Formula 1 may be represented by the following Formula 2-1 or 2-2.

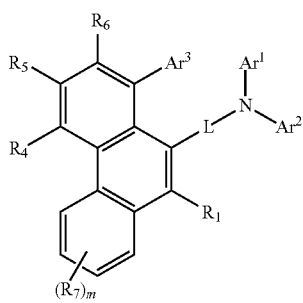

Formula 2-1

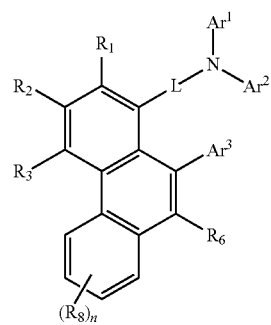

Formula 2-2

In Formulae 2-1 and 2-2, $R_7$ and $R_8$ may be each independently a hydrogen atom, a deuterium atom, a halogen atom, a cyano group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted alkoxy group having 1 to 20 carbon atoms, a substituted or unsubstituted alkylthio group having 1 to 20 carbon atoms, or a substituted or unsubstituted silyl group having 1 to 40 carbon atoms, m and n may be each independently an integer of 0 to 4, and L, $Ar_1$ to $Ar_3$, and $R_1$ to $R_6$ may be the same as respectively defined with respect to Formula 1.

In an embodiment, the monoamine compound represented by Formula 1 may be represented by the following Formula 3.

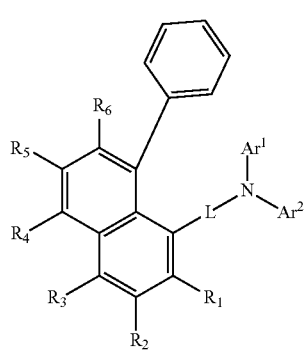

Formula 3

In Formula 3, L, $Ar_1$, $Ar_2$, and $R_1$ to $R_6$ may be the same as respectively defined with respect to Formula 1.

In an embodiment, the monoamine compound represented by Formula 1 may be represented by the following Formula 4.

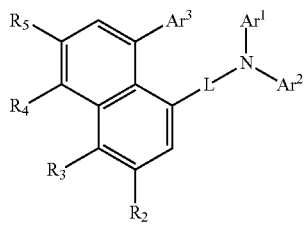

Formula 4

In Formula 4, the other pair of $R_2$ and $R_3$, or $R_4$ and $R_5$, which do not form a substituted or unsubstituted benzene ring, may each be a hydrogen atom, and L and $Ar_1$ to $Ar_3$ may be the same as respectively defined with respect to Formula 1.

In an embodiment, the plurality of organic layers may include a hole transport region on the first electrode, an emission layer on the hole transport region, and an electron transport region on the emission layer. The hole transport region may include the monoamine compound represented by the above Formula 1. In an embodiment, the emission layer may be configured to emit blue light with a wavelength range of about 440 nm to about 490 nm.

According to an embodiment of the present disclosure, there may be provided a monoamine compound represented by the above Formula 1.

BRIEF DESCRIPTION OF THE FIGURES

The accompanying drawings are included to provide a further understanding of the subject matter of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Figure 1:
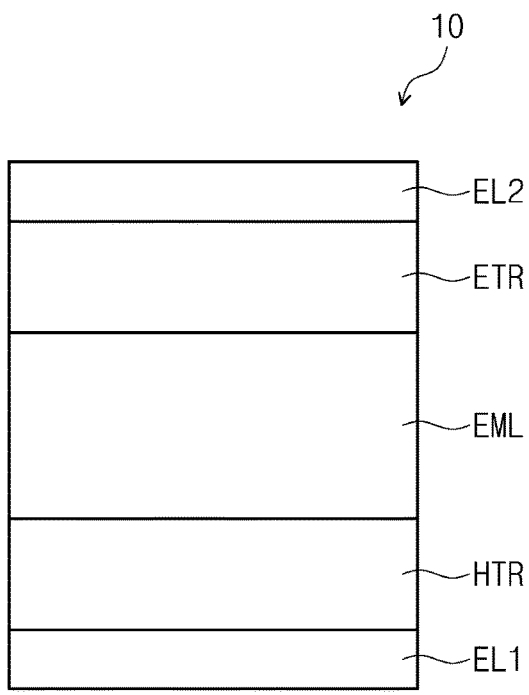
FIG. 1 is a schematic cross-sectional view of an organic electroluminescence device according to an embodiment of the present disclosure.

The subject matter of the present disclosure may have various modifications and may be embodied in different forms, and example embodiments will be explained in more detail with reference to the accompany drawings. However, the subject matter of the present disclosure should not be construed as limited to the embodiments set forth herein. Rather, it should be understood that the scope of the present disclosure includes all modification, equivalents and alternatives within the spirit and scope of the present disclosure as hereinafter claimed.

Like reference numerals refer to like elements for explaining each drawing. In the drawings, the sizes of elements may be enlarged for clarity of illustration. It will be understood that, although the terms first, second, etc., may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be understood that the terms "comprise" and/or "have," when used in this specification, specify the presence of stated features, numerals, steps, operations, elements, parts, or a combination thereof, but do not preclude the presence or addition of one or more other features, numerals, steps, operations, elements, parts, or a combination thereof.

In the present disclosure, when a layer, a film, a region, a plate, etc., is referred to as being "on" or "above" another part, it can be "directly on" the other part, or intervening parts may also be present. Similarly, when a layer, a film, a region, a plate, etc., is referred to as being "under" or "below" another part, it can be "directly under" or "directly below" the other part, or intervening parts may also be present. Furthermore, when used in this specification, the term "disposed on" may encompass both orientations of above and below.

In the present disclosure, the term "substituted or unsubstituted" may refer to an unsubstituted functional group or a functional group substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring, an aryl group and a heterocyclic group. In addition, each of the substituent illustrated above may be substituted or unsubstituted. For example, a biphenyl group may be interpreted as an aryl group, or a phenyl group substituted with a phenyl group.

In the present disclosure, examples of a halogen atom may include a fluorine atom, a chlorine atom, a bromine atom, and/or an iodine atom.

In the present disclosure, the alkyl group may have a linear, branched or cyclic form. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without being limited thereto.

In the present disclosure, the term "hydrocarbon ring" refers to any functional group or substituent derived from an aliphatic hydrocarbon ring. The hydrocarbon ring may be a saturated hydrocarbon ring including 5 to 20 carbon atoms for forming a ring.

In the present disclosure, the term "aryl group" refers to any functional group or substituent derived from an aromatic hydrocarbon ring. The aryl group may be a monocyclic aryl or a polycyclic aryl. The carbon number of the aryl group for forming a ring may be 6 to 30, 6 to 20, or 6 to 15. Examples of the aryl group may include phenyl, naphthyl, fluorenyl, anthracenyl, phenanthryl, biphenyl, terphenyl, quaterphenyl, quinophenol, sexiphenyl, triphenylenyl, pyrenyl, benzofluoranthenyl, chrysenyl, etc., without being limited thereto.

In the present disclosure, the fluorenyl group may be substituted, and two substituents may combine with each other to form a spiro structure. Examples of the substituted fluorenyl group may include the following groups, without being limited thereto.

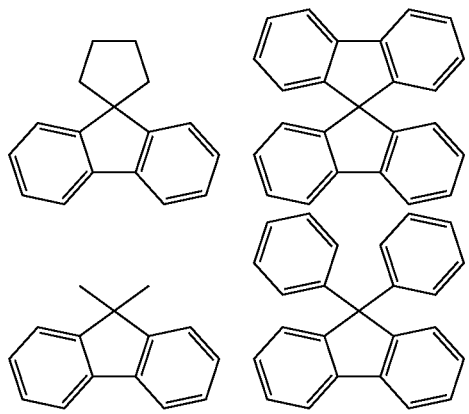

In the present disclosure, the heteroaryl group may include B, O, N, P, Si, and/or S as a heteroatom. When the heteroaryl group includes two or more heteroatoms, these heteroatoms may be the same or different from each other. The heteroaryl group may be monocyclic heteroaryl or polycyclic heteroaryl. The carbon number of the heteroaryl group for forming a ring may be 2 to 30, 2 to 20, or 2 to 10. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-aryl carbazole, N-heteroaryl carbazole, N-alkyl carbazole, benzoxazole, benzoimidazole, benzothiazole, benzocarbazole, benzothiophene, dibenzothiophene, thienothiophene, benzofuran, phenanthroline, thiazole, isoxazole, oxadiazole, thiadiazole, phenothiazine, dibenzosilole, dibenzofuran, etc., without being limited thereto.

In the present disclosure, the above explanation on the aryl group may be applied to the arylene group, except that the arylene group is divalent. The above explanation on the heteroaryl group may be applied to the heteroarylene group, except that the heteroarylene group is divalent.

In the present disclosure, the silyl group may include alkylsilyl and arylsilyl. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc., without being limited thereto.

In the present disclosure, the thio group may include alkylthio and arylthio.

In the present disclosure, the oxy group may include alkoxy and aryloxy. The alkoxy group may have a linear, branched or cyclic form. The carbon number of the alkoxy group is not specifically limited, but may be 1 to 20 or 1 to 10, for example. Examples of the oxy group may include methoxy, ethoxy, n-propoxy, isopropoxy, butoxy, pentyloxy, hexyloxy, octyloxy, nonyloxy, decyloxy, benzyloxy, etc., without being limited thereto.

In the present disclosure, the above-described examples of the alkyl group may be applied to the alkyl group in alkylthio and alkylsilyl.

In the present disclosure, the above-described examples of the aryl group may be applied to the aryl group in the arylthio group and the arylsilyl group.

In the present disclosure, a direct linkage may refer to a single bond.

FIG. 1 is a schematic cross-sectional view illustrating an organic electroluminescence device according to an embodiment of the present disclosure. An organic electroluminescence device 10 according to an embodiment of the present disclosure may include a first electrode EL1, a hole transport region HTR, an emission layer EML, an electron transport region ETR, and a second electrode EL2, laminated (e.g., stacked) in the stated order.

Figure 2:
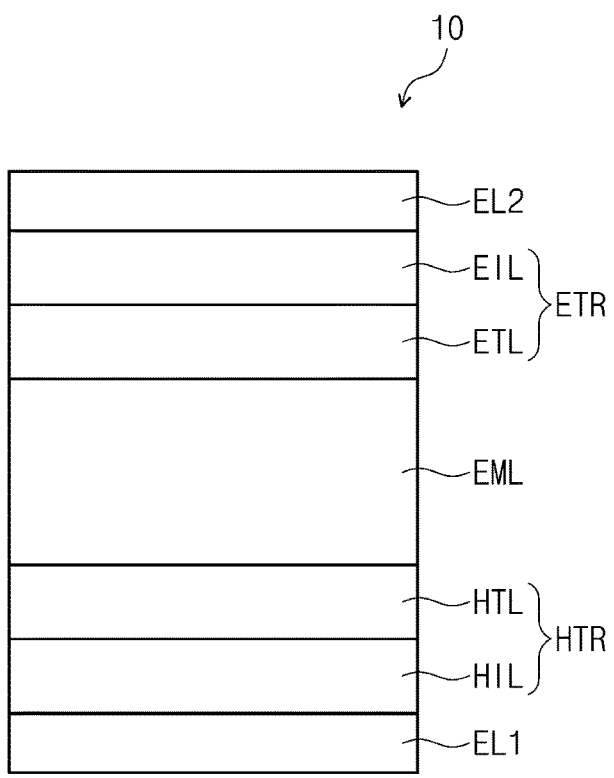
FIG. 2 is a schematic cross-sectional view of an organic electroluminescence device according to an embodiment of the present disclosure.
Figure 3:
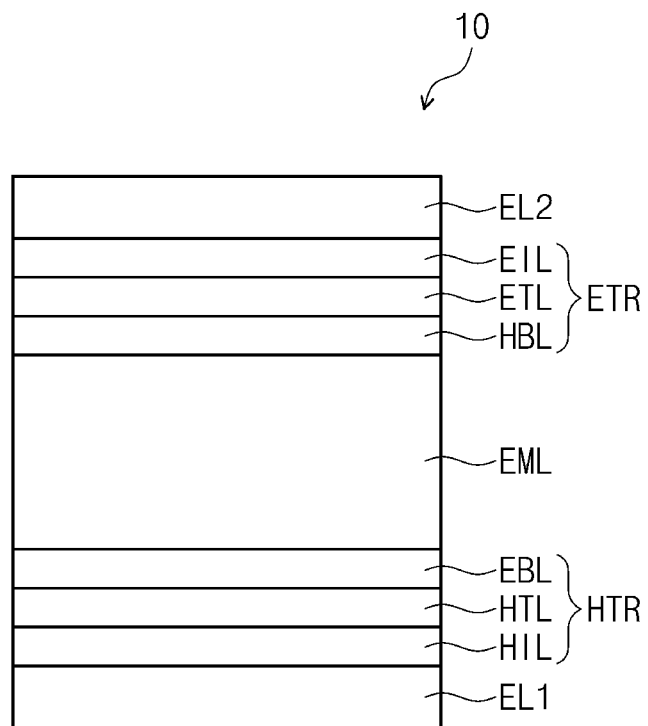
FIG. 3 is a schematic cross-sectional view of an organic electroluminescence device according to an embodiment of the present disclosure.

Comparing with FIG. 1, FIG. 2 shows a schematic cross-sectional view illustrating an organic electroluminescence device 10 according to an embodiment of the present disclosure, in which a hole transport region HTR includes a hole injection layer HIL and a hole transport layer HTL, and an electron transport region ETR includes an electron injection layer EIL and an electron transport layer ETL. Furthermore, comparing with FIG. 1, FIG. 3 shows a schematic cross-sectional view illustrating an organic electroluminescence device 10 according to an embodiment of the present disclosure, in which a hole transport region HTR includes a hole injection layer HIL, a hole transport layer HTL and an electron blocking layer EBL, and an electron transport region ETR includes an electron injection layer EIL, an electron transport layer ETL and a hole blocking layer HBL.

The first electrode EL1 has conductivity. The first electrode EL1 may be formed by a metal alloy or a conductive compound. The first electrode EL1 may be an anode. The first electrode EL1 may also be a pixel electrode. The first electrode EL1 may be a transmissive electrode, a transflective electrode, or a reflective electrode. When the first electrode EL1 is the transmissive electrode, the first electrode EL1 may include a transparent metal oxide such as indium tin oxide (ITO), indium zinc oxide (IZO), zinc oxide (ZnO), and/or indium tin zinc oxide (ITZO). When the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed utilizing the above materials, and a transparent conductive layer formed utilizing ITO, IZO, ZnO, and/or ITZO. For example, the first electrode EL1 may have a triple-layer structure of ITO/Ag/ITO. However, embodiments of the present disclosure are not limited thereto. The thickness of the first electrode EL1 may be from about 1,000 Å to about 10,000 Å, for example, from about 1,000 Å to about 3,000 Å.

In an organic electroluminescence device 10 according to an embodiment of the present disclosure, at least one of the organic layers included in the hole transport region HTR, the emission layer EML, and the electron transport region ETR may include a monoamine compound represented by Formula 1.

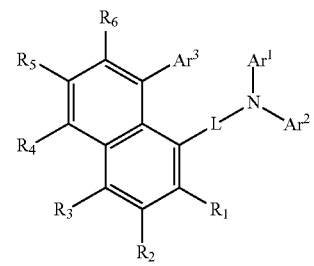

Formula 1

In Formula 1, L may be a direct linkage, an arylene group, or a heteroarylene group. The arylene group may be a substituted or unsubstituted arylene group having 6 to 30 carbon atoms for forming a ring. The heteroarylene group may be a substituted or unsubstituted heteroarylene group having 2 to 30 carbon atoms for forming a ring. For example, L may be a substituted or unsubstituted phenylene group, a substituted or unsubstituted divalent biphenyl group, or a substituted or unsubstituted dibenzofuranylene group. The substituted or unsubstituted phenylene group may be a substituted or unsubstituted o-phenylene group, a substituted or unsubstituted m-phenylene group, or a substituted or unsubstituted p-phenylene group. For example, the substituted or unsubstituted phenylene group may be a p-phenylene group. The p-phenylene group may be unsubstituted. In the present disclosure, o-, m- and p-, when preceding a compound name, may refer to ortho, meta, and para, respectively.

$Ar_1$ and $Ar_2$ may be each independently an aryl group or a heteroaryl group. The aryl group may be a substituted or unsubstituted aryl group having 6 to 30 carbon atoms for forming a ring. The heteroaryl group may be a substituted or unsubstituted heteroaryl group having 2 to 30 carbon atoms for forming a ring. For example, $Ar_1$ and $Ar_2$ may be each independently a substituted or unsubstituted phenyl group, a substituted or unsubstituted biphenyl group, a substituted or unsubstituted fluorenyl group, a substituted or unsubstituted dibenzofuranyl group, or a substituted or unsubstituted dibenzothiophenyl group. $Ar_1$ and $Ar_2$ may each be unsubstituted. When $Ar_1$ and $Ar_2$ are each substituted, they may be substituted with a phenyl group or a naphthyl group. For example, $Ar_1$ and $Ar_2$ may be each independently a phenyl group substituted with a naphthyl group, or a fluorenyl group substituted with a phenyl group. $Ar_1$ and $Ar_2$ may not be substituted with an amino group.

$Ar_3$ may be an aryl group or a heteroaryl group. The aryl group may be a substituted or unsubstituted aryl group having 6 to 30 carbon atoms for forming a ring. The heteroaryl group may be a substituted or unsubstituted heteroaryl group having 2 to 30 carbon atoms for forming a ring. For example, $Ar_3$ may be a substituted or unsubstituted phenyl group, a substituted or unsubstituted biphenyl group, or a substituted or unsubstituted naphthyl group. In one embodiment, $Ar_3$ may be an unsubstituted phenyl group.

$R_1$ to $R_6$ may be each independently a hydrogen atom, a deuterium atom, a halogen atom, a cyano group, an alkyl group, an aryl group, a heteroaryl group, an alkoxy group, an alkylthio group, or a silyl group. The alkyl group may be a substituted or unsubstituted alkyl group having 1 to 20 carbon atoms. The aryl group may be a substituted or unsubstituted aryl group having 6 to 30 carbon atoms for forming a ring, and the heteroaryl group may be a substituted or unsubstituted heteroaryl group having 2 to 30 carbon atoms for forming a ring. The alkoxy group may be a substituted or unsubstituted alkoxy group having 1 to 20 carbon atoms, the alkylthio group may be a substituted or unsubstituted alkylthio group having 1 to 20 carbon atoms, and the silyl group may be a substituted or unsubstituted silyl group having 1 to 40 carbon atoms. In one embodiment, $R_1$ may be a hydrogen atom, a deuterium atom, a halogen atom, a cyano group, a substituted or unsubstituted alkyl group having 1 to 20 carbon atoms, a substituted or unsubstituted alkoxy group having 1 to 20 carbon atoms, a substituted or unsubstituted alkylthio group having 1 to 20 carbon atoms, or a substituted or unsubstituted silyl group having 1 to 40 carbon atoms. For example, $R_1$ to $R_6$ may be each independently a hydrogen atom. When one or more of $R_1$ to $R_6$ are each independently a silyl group, they may be a trialkylsilyl group.

Two substituents selected from $R_2$ and $R_3$, or $R_4$ and $R_5$ may combine with each other to form a substituted or unsubstituted benzene ring. That is, $R_2$ and $R_3$, or $R_4$ and $R_5$ may combine with each other to form a substituted or unsubstituted benzene ring. In one embodiment, $R_1$ to $R_6$ may be the same or different from each other.

The monoamine compound represented by Formula 1 may be represented by the following Formula 2-1 or 2-2.

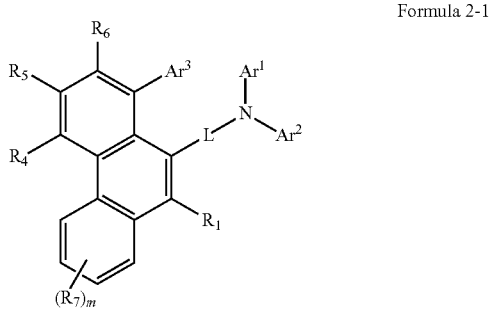

Formula 2-1

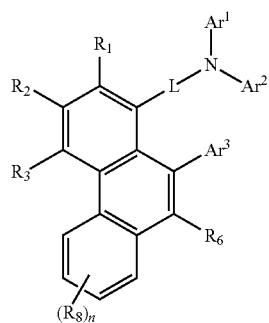

Formula 2-2

In Formulae 2-1 and 2-2, $R_7$ and $R_8$ may be each independently a hydrogen atom, a deuterium atom, a halogen atom, a cyano group, an alkyl group, an aryl group, a heteroaryl group, an alkoxy group, an alkylthio group, or a silyl group. The alkyl group may be a substituted or unsubstituted alkyl group having 1 to 20 carbon atoms. The aryl group may be a substituted or unsubstituted aryl group having 6 to 30 carbon atoms for forming a ring, and the heteroaryl group may be a substituted or unsubstituted heteroaryl group having 2 to 30 carbon atoms for forming a ring. The alkoxy group may be a substituted or unsubstituted alkoxy group having 1 to 20 carbon atoms, the alkylthio group may be a substituted or unsubstituted alkylthio group having 1 to 20 carbon atoms, and the silyl group may be a substituted or unsubstituted silyl group having 1 to 40 carbon atoms. In one embodiment, $R_7$ and $R_8$ may be each independently a hydrogen atom, a deuterium atom, a halogen atom, a cyano group, a substituted or unsubstituted alkyl group having 1 to 20 carbon atoms, a substituted or unsubstituted alkoxy group having 1 to 20 carbon atoms, a substituted or unsubstituted alkylthio group having 1 to 20 carbon atoms, or a substituted or unsubstituted silyl group having 1 to 40 carbon atoms. For example, $R_7$ and $R_8$ may be each independently a hydrogen atom or a deuterium atom.

In Formulae 2-1 and 2-2, m and n may be each independently an integer of 0 to 4. For example, both of m and n may be 0. When m or n is an integer of 2 or more, a plurality of $R_7$ or $R_8$ may be the same or different from each other.

In Formulae 2-1 and 2-2, L, $Ar_1$ to $Ar_3$, and $R_1$ to $R_6$ may be the same as respectively defined with respect to Formula 1.

The monoamine compound represented by Formula 1 may be represented by the following Formula 3.

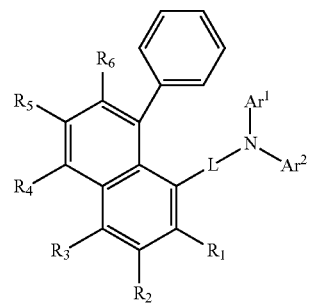

Formula 3

Formula 3 is an embodiment of Formula 1 in which $Ar_3$ is an unsubstituted phenyl group. In Formula 3, L, $Ar_1$, $Ar_2$, and $R_1$ to $R_6$ may be the same as respectively defined with respect to Formula 1.

The monoamine compound represented by Formula 1 may be represented by the following Formula 4.

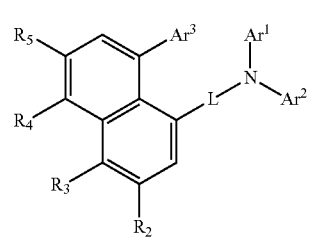

Formula 4

In Formula 4, two substituents selected from $R_2$ and $R_3$, or $R_4$ and $R_5$ may combine with each other to form an unsubstituted benzene ring, and the other two substituents may be each independently a hydrogen atom. For example, the monoamine compound represented by Formula 4 may be represented by the following Formula 4-1 or 4-2.

Formula 4-1
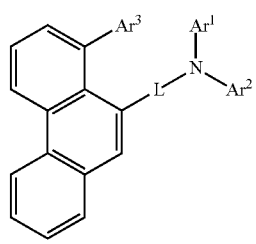
Formula 4-2
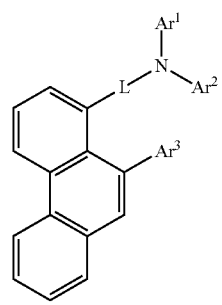
In Formulae 4, 4-1 and 4-2, L and Ar$_1$ to Ar$_3$ may be the same as respectively defined with respect to Formula 1.
The monoamine compound according to an embodiment of the present disclosure may be any one of compounds represented in the following Compound Group 1.
Compound Group 1
1
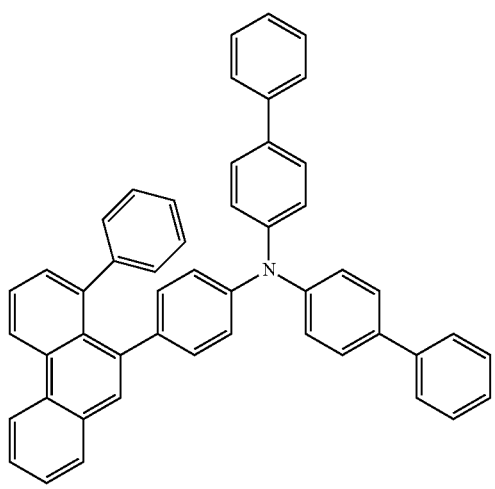
2
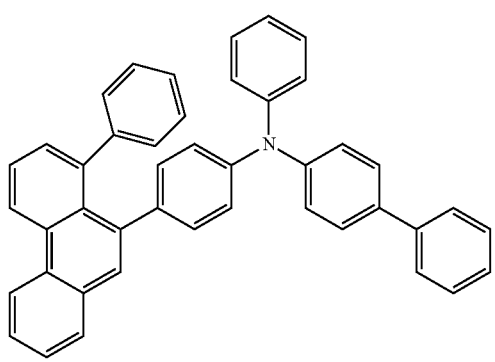
3
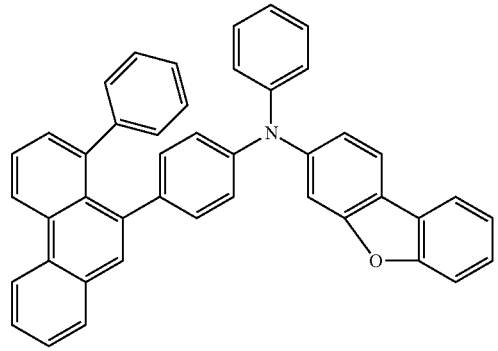
4
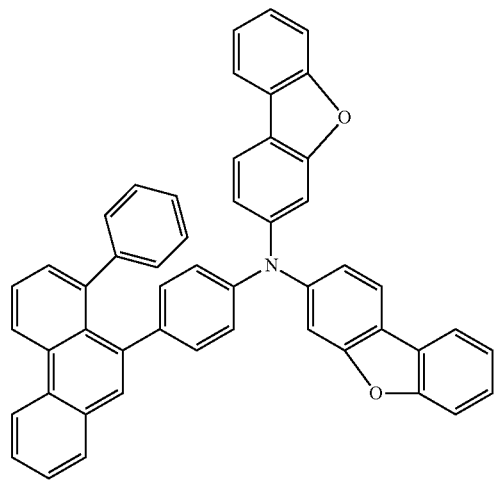
5
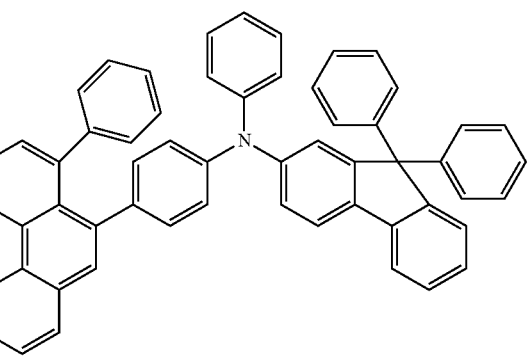
6
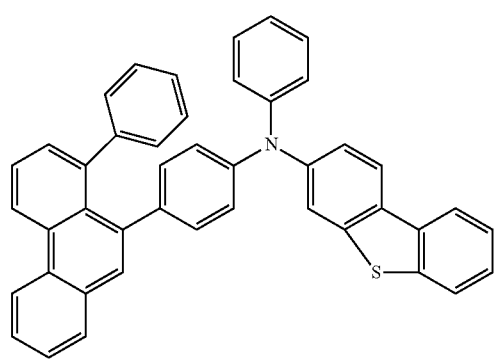

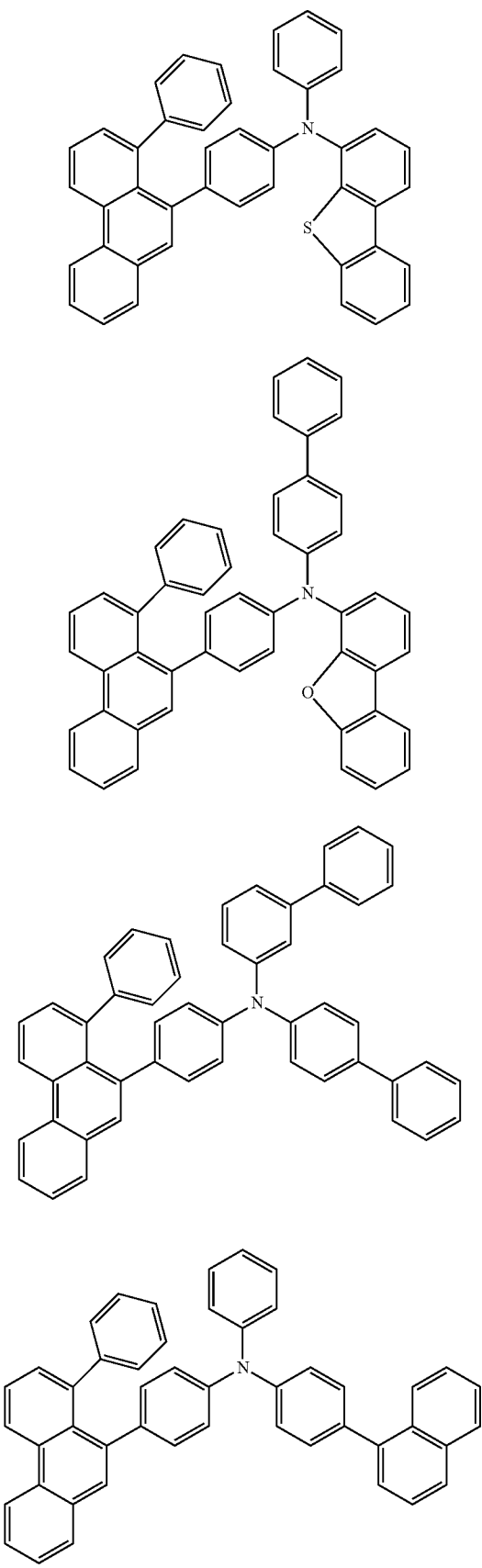
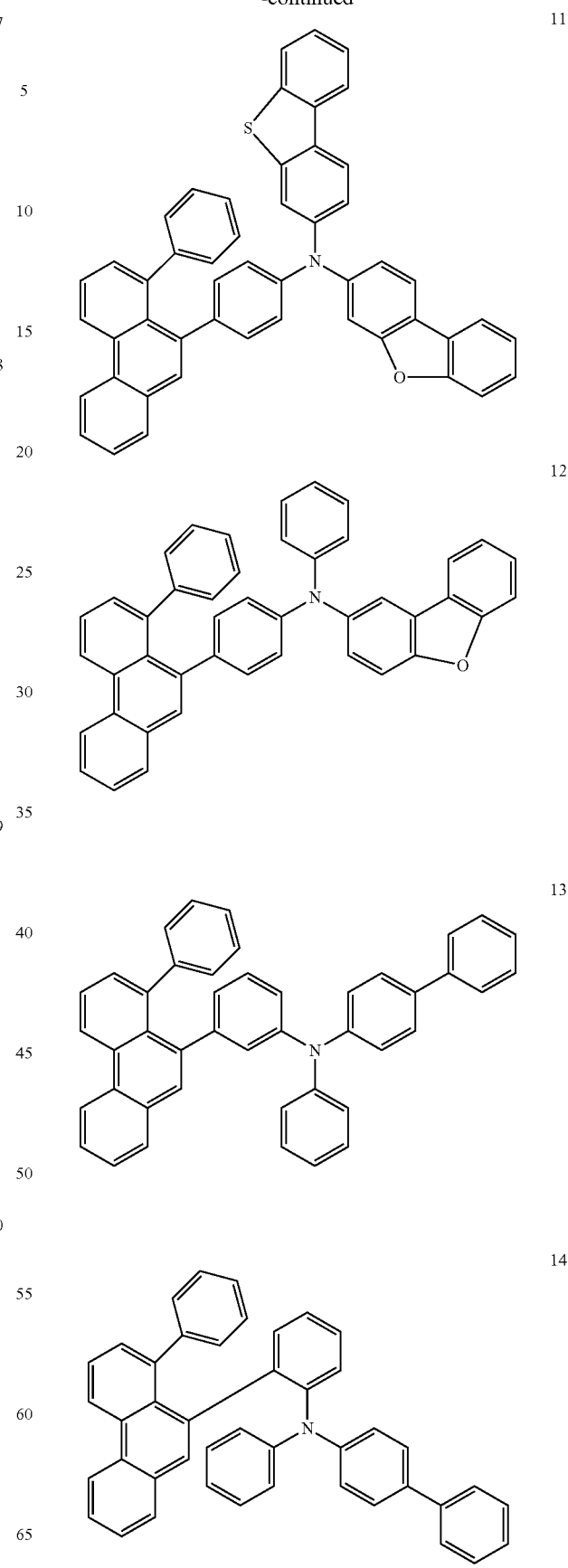

15
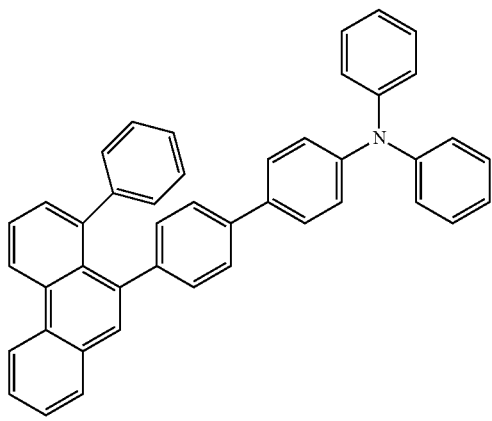
16
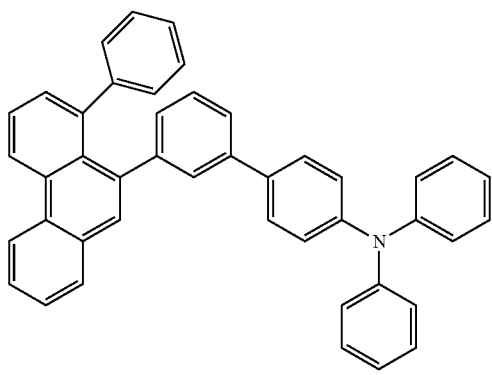
17
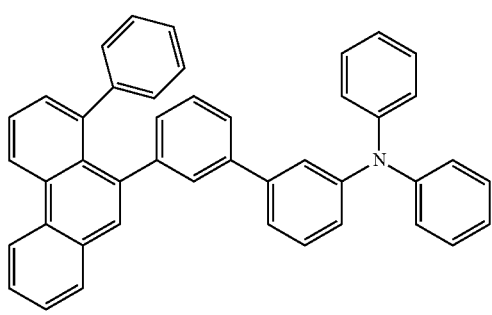
18
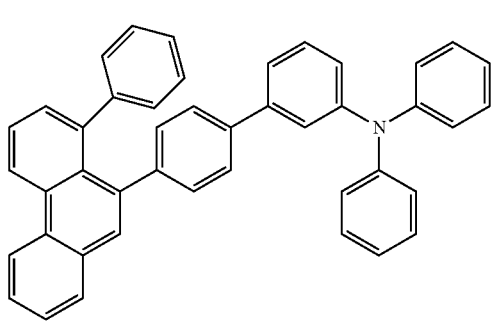
19
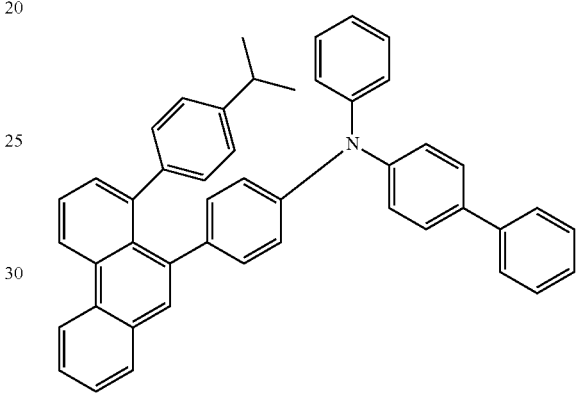
20
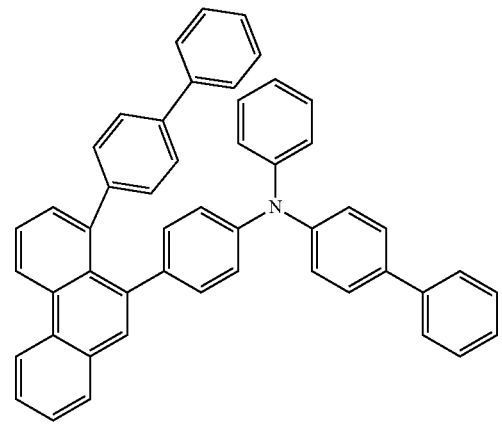
21
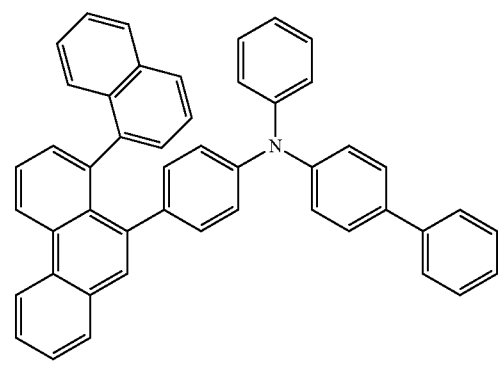
22

23
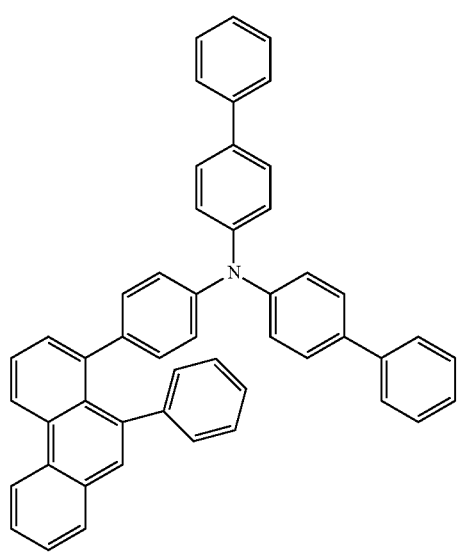
24
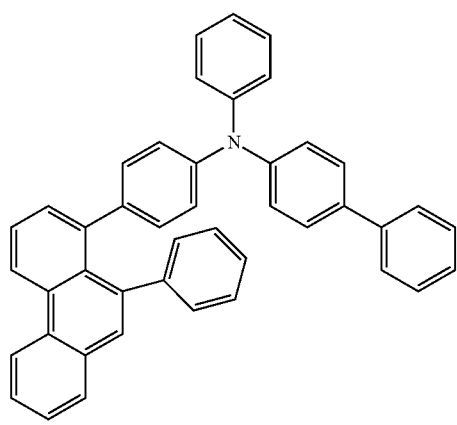
25
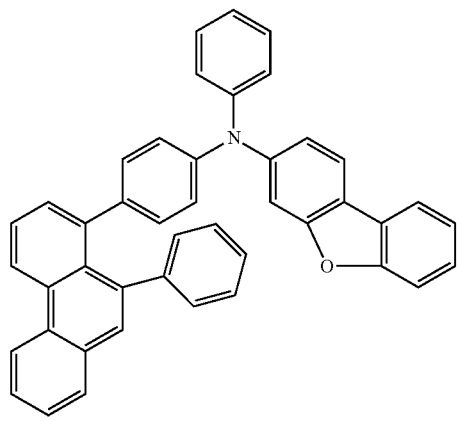
26
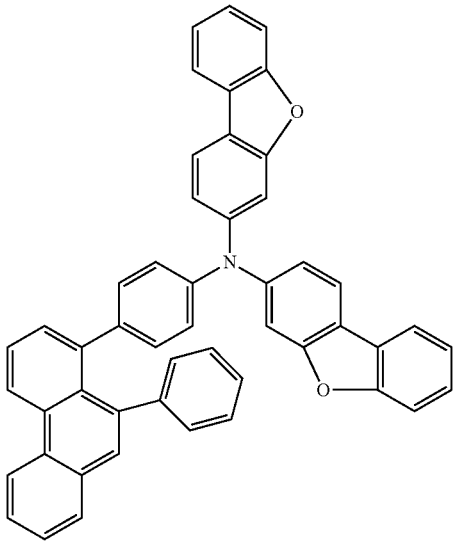
27
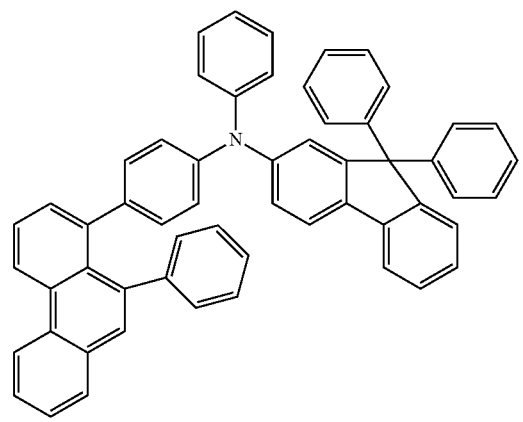
28
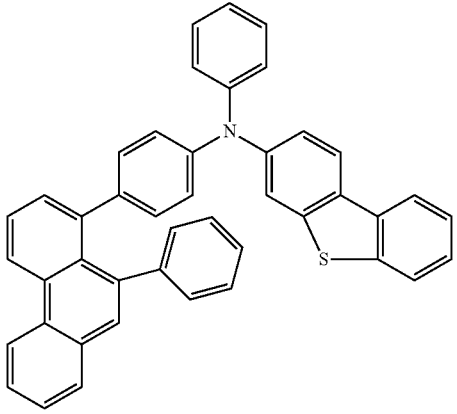

29
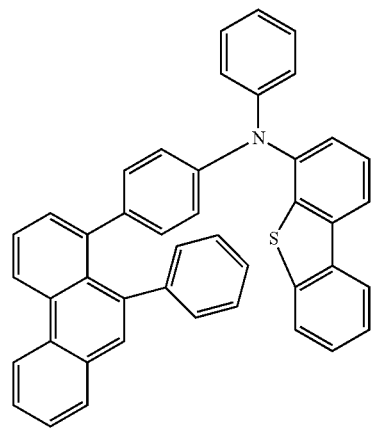
30
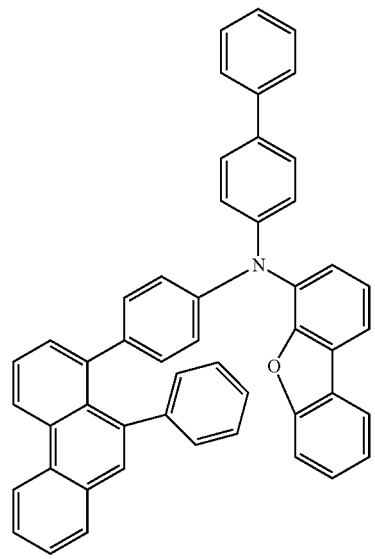
31
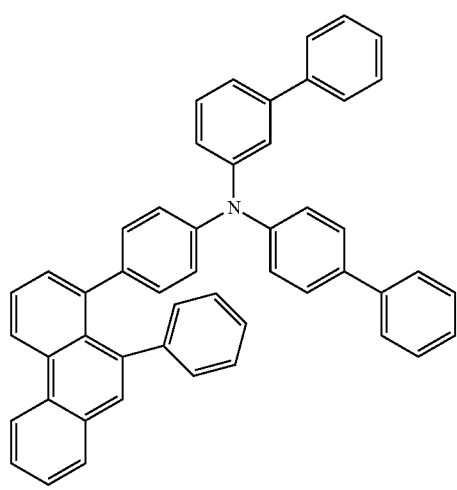
32
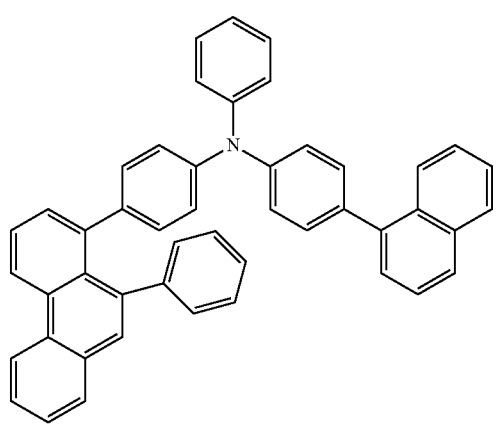
33
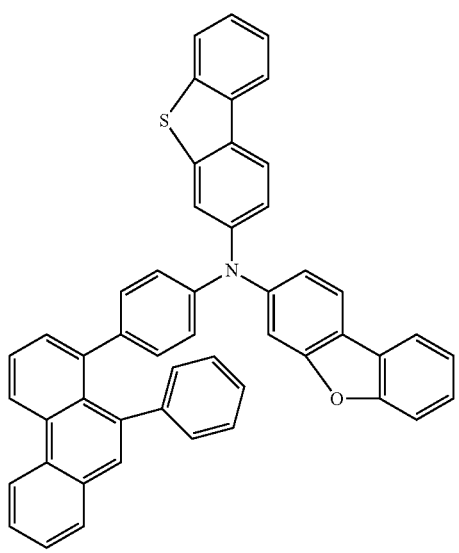
34
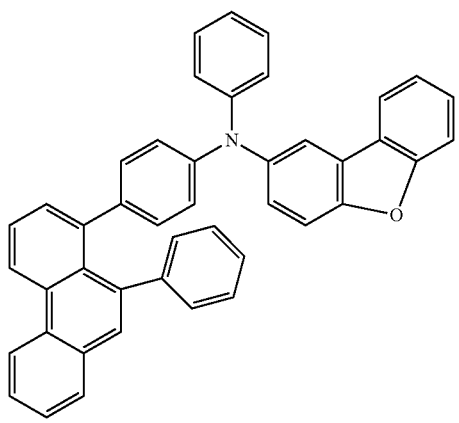

35
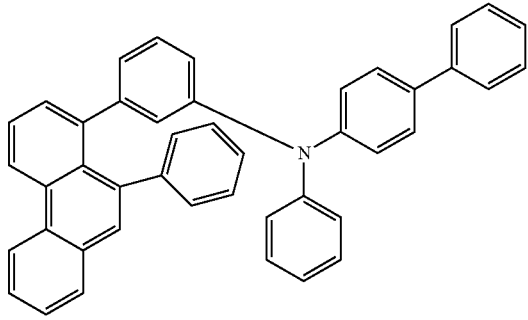
36
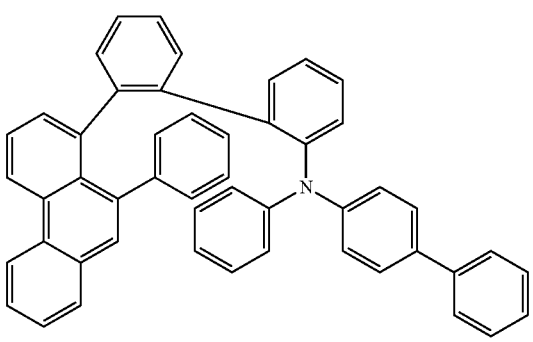
37
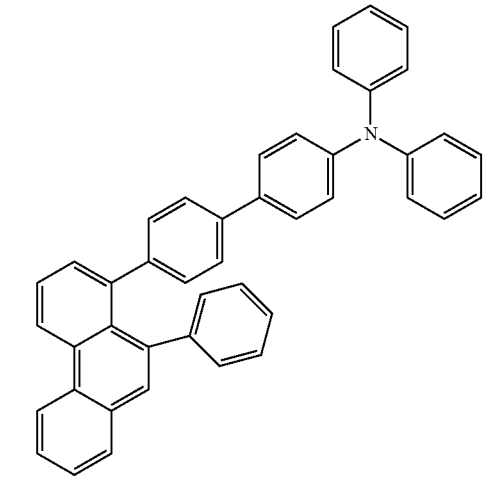
39
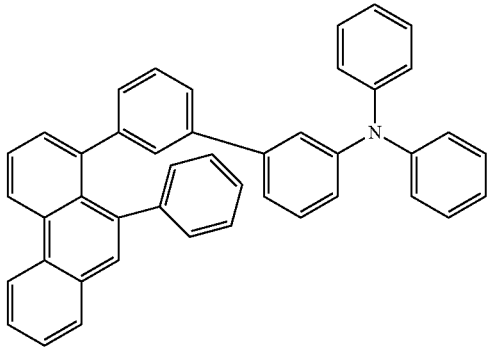
40
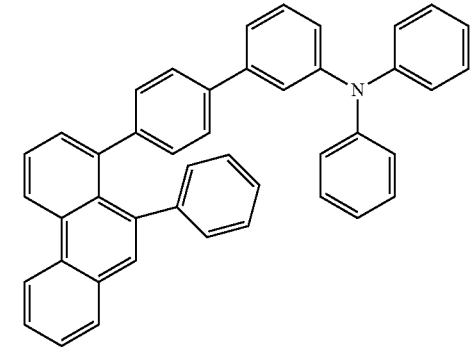
41
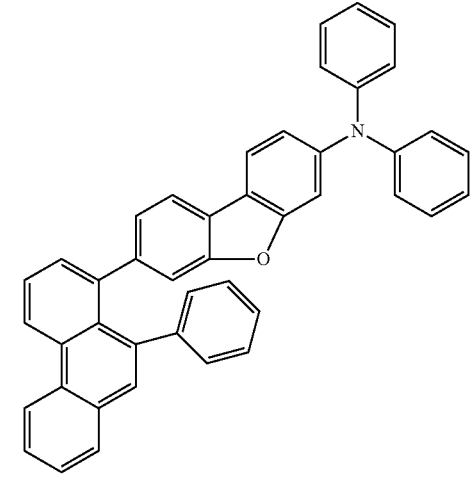
42
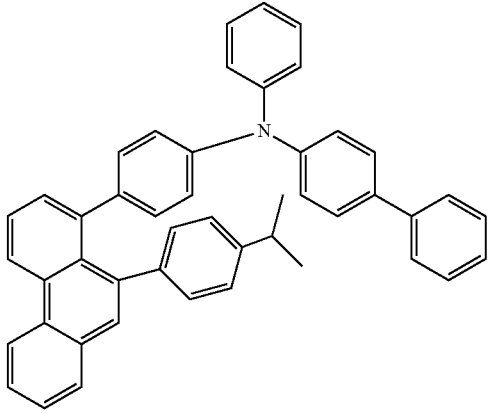

-continued

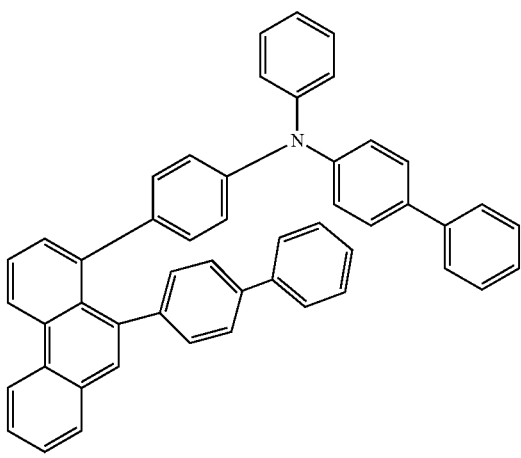

44

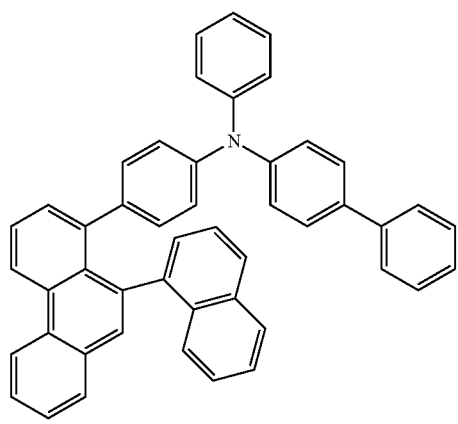

44

In the organic electroluminescence device 10 according to embodiments of the present disclosure as shown in FIGS. 1 to 3, the hole transport region HTR may include one or more of the monoamine compound represented in Compound Group 1. Also, the hole transport region HTR may further include a suitable (e.g., known) material in addition to the monoamine compound represented in Compound Group 1.

In the organic electroluminescence device 10 according to an embodiment of the present disclosure, the hole transport region HTR may include the above-described monoamine compound according to an embodiment of the present disclosure. When the hole transport region HTR includes a plurality of organic layers, the monoamine compound according to an embodiment of the present disclosure may be included in the organic layer adjacent to the emission layer EML. For example, the monoamine compound according to an embodiment of the present disclosure may be included in the hole transport layer HTL of the hole transport region HTR.

In one embodiment, when the organic electroluminescence device 10 according to an embodiment of the present disclosure includes a hole injection layer HIL and a hole transport layer HTL in the hole transport region HTR, the monoamine compound according to an embodiment of the present disclosure may be included in the hole transport layer HTL.

The hole transport region HTR is disposed on the first electrode EL1. The hole transport region HTR may include a hole injection layer HIL, a hole transport layer HTL, a hole buffer layer, and/or an electron blocking layer EBL.

The hole transport region HTR may have a single layer formed utilizing a single material, a single layer formed utilizing a plurality of different materials, or a multilayer structure including a plurality of layers formed utilizing a plurality of different materials.

For example, the hole transport region HTR may have a single layer structure of a hole injection layer HIL or a hole transport layer HTL, or may have a single layer structure formed utilizing a hole injection material and a hole transport material. In addition, the hole transport region HTR may have a single layer structure formed utilizing a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated (e.g., stacked) in the stated order from the first electrode EL1, without being limited thereto.

The hole transport region HTR may be formed utilizing various suitable methods such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may further include carbazole derivatives (such as N-phenyl carbazole, polyvinyl carbazole, etc.), fluorine-based derivatives, N,N'-bis(3-methylphenyl)-N,N'-diphenyl-[1,1-biphenyl]-4,4'-diamine (TPD), triphenylamine-based derivatives (such as 4,4',4''-tris(N-carbazolyl)triphenylamine (TCTA)), N,N'-di(naphthalen-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), α-NPD, 1,3-bis(N-carbazolyl)benzene (mCP), etc.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be obtained without substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. The p-dopant may be at least one selected from quinone derivatives, metal oxides, and cyano group-containing compounds, without being limited thereto. For example, non-limiting examples of the p-dopant may include quinone derivatives (such as tetracyanoquinodimethane (TCNQ), and 2,3,5,6-tetrafluoro-tetracyanoquinodimethane (F4-TCNQ)), and metal oxides (such as tungsten oxide and molybdenum oxide), without being limited thereto.

As described above, the hole transport region HTR may further include a hole buffer layer and/or an electron blocking layer EBL in addition to the hole injection layer HIL and the hole transport layer HTL. The hole buffer layer may compensate an optical resonance distance according to the wavelength of light emitted from the emission layer EML and increase light emission efficiency. Materials included in the hole transport region HTR may be utilized as materials included in the hole buffer layer. The electron blocking layer EBL is a layer preventing or reducing electron injection from the electron transport region ETR into the hole transport region HTR.

The emission layer EML is disposed on the hole transport region HTR. The thickness of the emission layer EML may be, for example, from about 100 Å to about 1,000 Å, or from about 100 Å to about 300 Å. The emission layer EML may have a single layer formed utilizing a single material, a single layer formed utilizing a plurality of different materials, or a multilayer structure having a plurality of layers formed utilizing a plurality of different materials.

In the organic electroluminescence device 10 according to an embodiment of the present disclosure, the emission layer EML may include at least one selected from anthracene derivatives, pyrene derivatives, fluoranthene derivatives, chrysene derivatives, dihydrobenzanthracene derivatives, and triphenylene derivatives. In one embodiment, the emission layer EML may include at least one selected from anthracene derivatives and pyrene derivatives.

The emission layer EML may include anthracene derivatives represented by the following Formula C.

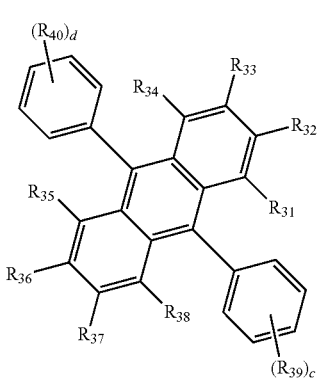

Formula C

In Formula C, $R_{31}$ to $R_{40}$ may be each independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a ring formed by combining adjacent groups with each other. Also, adjacent groups selected from among $R_{31}$ to $R_{40}$ may combine with each other to form a saturated hydrocarbon ring or an unsaturated hydrocarbon ring.

In Formula C, c and d may be each independently an integer of 0 to 5.

The compound represented by Formula C may be represented by any one of the following Compounds 3-1 to 3-6.

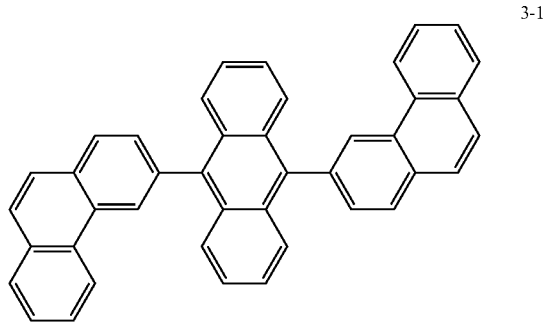

3-1

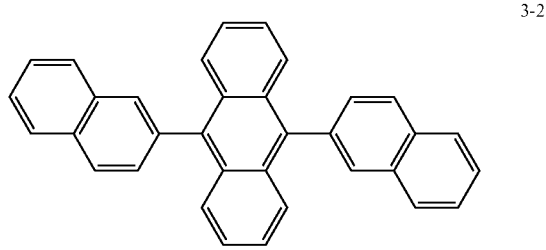

3-2

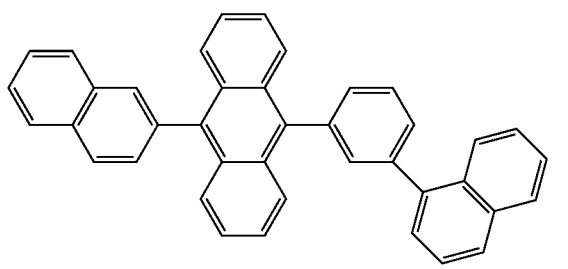

3-3

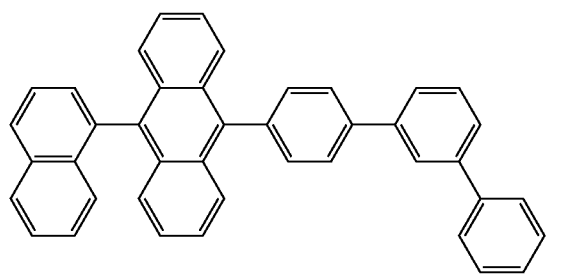

3-4

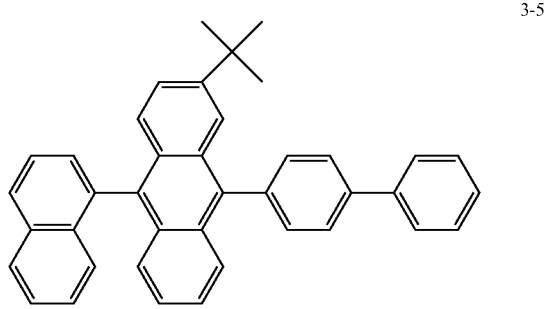

3-5

-continued 3-6

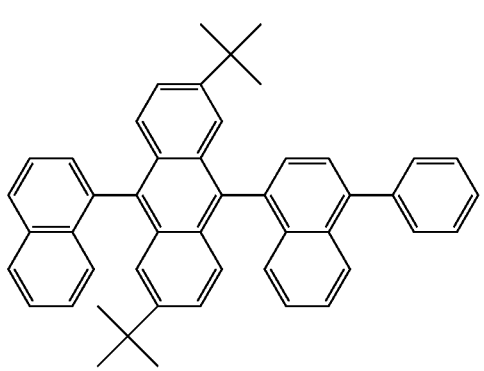

In the organic electroluminescence device 10 according to embodiments of the present disclosure as shown in FIGS. 1 to 3, the emission layer EML may include a host and a dopant, and the emission layer EML may include the above-described compound represented by Formula C as a host material.

The emission layer EML may further include a suitable (e.g., known) material as a host material. For example, the emission layer EML may include, as a host material, at least one selected from bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TcTa) and 1,3,5-tris(N-phenylbenzimidazole-2-yl)benzene (TPBi). However, embodiments of the present disclosure are not limited thereto. For example, tris(8-hydroxyquinolino)aluminum (Alq3), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO₃), octaphenylcyclotetrasiloxane (DPSiO₄), 2,8-bis(diphenylphosphoryl)dibenzofuran (PPF), etc., may be utilized as a host material.

In an embodiment, the emission layer EML may include, as a suitable (e.g., known) dopant material, styryl derivatives (for example, 1,4-bis[2-(3-N-ethylcarbazolyl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi), etc.), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.), etc.

The emission layer may emit any one of red light, green light or blue light. For example, the emission layer may emit blue light with a wavelength range of about 440 nm to about 490 nm.

In the organic electroluminescence device 10 according to embodiments of the present disclosure as shown in FIGS. 1 to 3, the electron transport region ETR is provided on the emission layer EML. The electron transport region ETR may include a hole blocking layer HBL, an electron transport layer ETL and/or an electron injection layer EIL, without being limited thereto.

The electron transport region ETR may have a single layer formed utilizing a single material, a single layer formed utilizing a plurality of different materials, or a multilayer structure having a plurality of layers formed utilizing a plurality of different materials.

For example, the electron transport region ETR may have a single layer structure of an electron injection layer EIL or an electron transport layer ETL, or a single layer structure formed utilizing an electron injection material and an electron transport material. In addition, the electron transport region ETR may have a single layer structure having a plurality of different materials, or a laminated structure of electron transport layer ETL/electron injection layer EIL, or hole blocking layer HBL/electron transport layer ETL/electron injection layer EIL, laminated (e.g., stacked) in the stated order from the emission layer EML, without being limited thereto. The thickness of the electron transport region ETR may be, for example, from about 1,000 Å to about 1,500 Å.

The electron transport region ETR may be formed utilizing various suitable methods such as a vacuum deposition method, a spin coating method, a cast method, a Langmuir-Blodgett (LB) method, an inkjet printing method, a laser printing method, and/or a laser induced thermal imaging (LITI) method.

When the electron transport region ETR includes the electron transport layer ETL, the electron transport region ETR may include anthracene derivatives. However, embodiments of the present disclosure are not limited thereto. For example, the electron transport region may include at least one selected from tris(8-hydroxyquinolinato)aluminum (Alq₃), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-Biphenyl-4-olato)aluminum (BAlq), berylliumbis (benzoquinolin-10-olate) (Bebq₂), 9,10-di(naphthalen-2-yl) anthracene (ADN), and a mixture thereof. The thickness of the electron transport layer ETL may be from about 100 Å to about 1,000 Å, for example, from about 150 Å to about 500 Å. If the thickness of the electron transport layer ETL satisfies the above-described ranges, satisfactory electron transport properties may be obtained without substantial increase of a driving voltage.

When the electron transport region ETR includes the electron injection layer EIL, the electron transport region ETR may be formed utilizing LiF, lithium quinolate (LIQ), Li₂O, BaO, NaCl, CsF, a metal in lanthanoides (such as Yb), and/or a metal halide (such as RbCl and/or RbI). However, embodiments of the present disclosure are not limited thereto. The electron injection layer EIL also may be formed utilizing a mixture material of an electron transport material and an insulating organo metal salt. The organo metal salt may be a material having an energy band gap of about 4 eV or more. For example, the organo metal salt may include a metal acetate, a metal benzoate, a metal acetoacetate, a metal acetylacetonate, and/or a metal stearate. The thickness of the electron injection layer EIL may be from about 1 Å to about 100 Å, for example, from about 3 Å to about 90 Å. When the thickness of the electron injection layer EIL satisfies the above described ranges, satisfactory electron injection properties may be obtained without inducing the substantial increase of a driving voltage.

The electron transport region ETR may include a hole blocking layer HBL, as described above. The hole blocking layer HBL may include, for example, at least one of 2,9-dimethyl-4,7-diphenyl-1,10-phenanthroline (BCP) or 4,7-diphenyl-1,10-phenanthroline (Bphen), without being limited thereto.

The second electrode EL2 is disposed on the electron transport region ETR. The second electrode EL2 may be a common electrode or a cathode. The second electrode EL2 may be a transmissive electrode, a transflective electrode or a reflective electrode. When the second electrode EL2 is the transmissive electrode, the second electrode EL2 may be formed utilizing transparent metal oxides, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayer structure including a reflective layer or a transflective layer formed utilizing the above-described materials and a transparent conductive layer formed utilizing ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In some embodiments, the organic electroluminescence device 10 according to an embodiment of the present disclosure may include a capping layer disposed on the second electrode EL2. The capping layer may include, for example, α-NPD, NPB, TPD, m-MTDATA, Alq3, CuPc, N4,N4,N4',N4'-tetra(biphenyl-4-yl)biphenyl-4,4'-diamine (TPD15), 4,4',4''-tris(carbazol-9-yl)-triphenylamine (TCTA), etc.

The above-described monoamine compound according to an embodiment of the present disclosure may also be included in organic layers other than the hole transport region HTR as a material for an organic electroluminescence device 10. The organic electroluminescence device 10 according to an embodiment of the present disclosure may include the above-described monoamine compound in at least one of the organic layers disposed between the first electrode EL1 and the second electrode EL2 or in the capping layer disposed on the second electrode EL2.

In the organic electroluminescence device 10, according to the application of a voltage to each of the first electrode EL1 and the second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

Hereinafter, the monoamine compound according to an embodiment of the present disclosure and the organic electroluminescence device according to an embodiment of the present disclosure including the monoamine compound will be explained in more detail with reference to specific embodiments and comparative embodiments. The following embodiments are illustrated only for assisting the understanding of the present disclosure, and the scope of the present disclosure is not limited thereto.

1. Synthesis Examples

The monoamine compound according to an embodiment of the present disclosure may be synthesized as follows, for example. However, the synthetic method of the monoamine compound according to an embodiment of the present disclosure is not limited thereto.

1-1. Synthesis of Compound 1

Compound 1, a monoamine compound according to an embodiment of the present disclosure, may be synthesized as shown in the following Reaction scheme 1, for example.

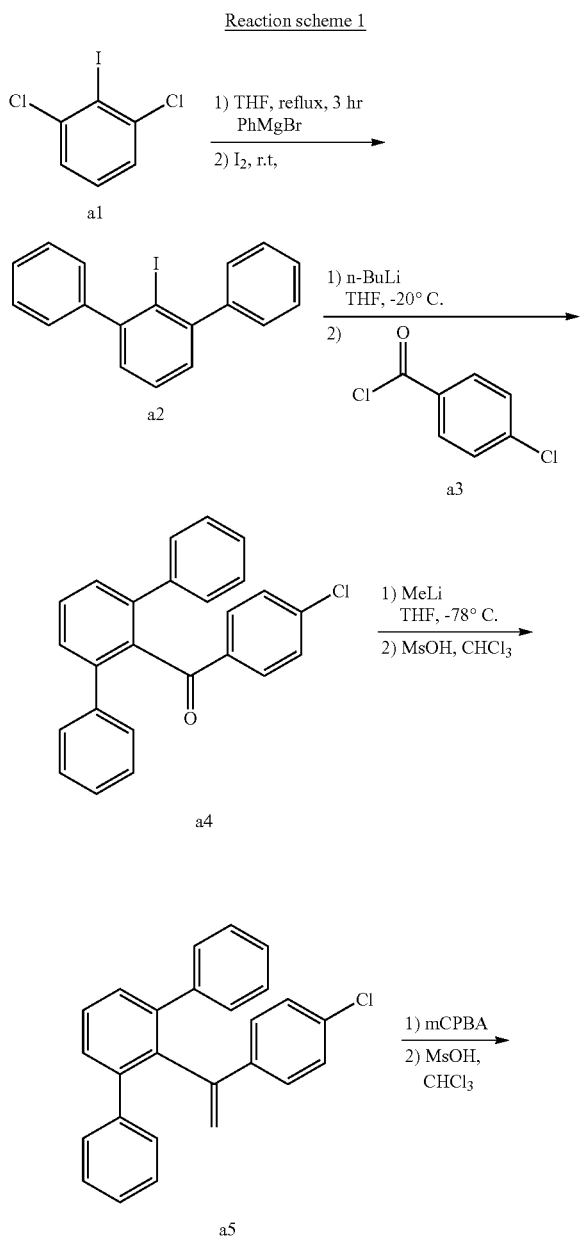

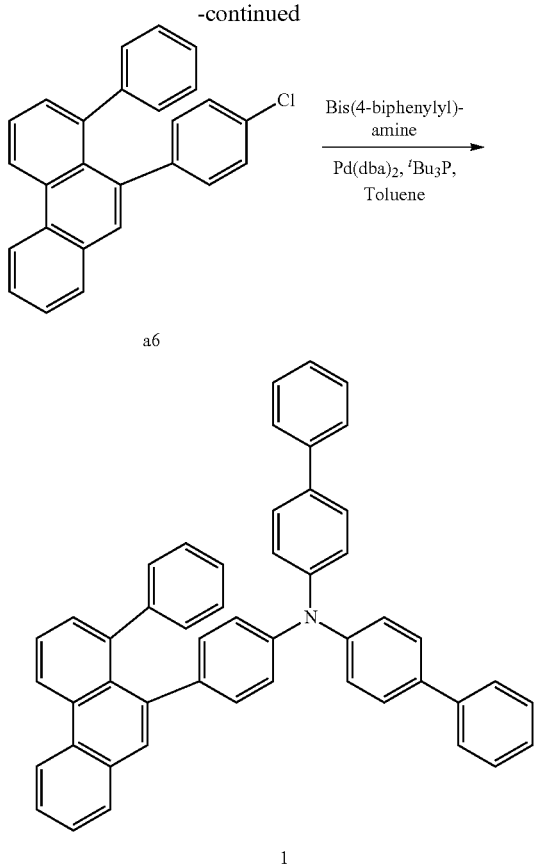

a6

1

Synthesis of Intermediate a2

Under an argon atmosphere, 1,3-dichloro-2-iodobenzene (a1) (25.0 g, 91.6 mmol) was added dropwise to tetrahydrofuran (180 mL). While stirring the resultant at about 40° C., phenyl magnesium bromide (27.5 mL, 27.5 mmol, 1 M tetrahydrofuran solution) was added dropwise thereto, and the mixture was heated to reflux for about 3 hours. After cooling the reaction solution to room temperature, iodine (34.9 g, 137 mmol) was added thereto, and the mixture was stirred for about 1 hour. The reaction solution was added with sodium thiosulfate, and then extracted with toluene. The extracted organic layer was dried over anhydrous magnesium sulfate and then concentrated. The residue was purified by silica gel chromatography to obtain Intermediate a2 (28.7 g, yield 88%).

Synthesis of Intermediate a4

Intermediate a2 (25.0 g, 70.0 mmol) was added dropwise to tetrahydrofuran (250 mL). While stirring the resultant at about −20° C., n-butyllithium (43.8 mL, 70.0 mmol, 1.6 M hexane solution) was added dropwise thereto, and the mixture was stirred for about 30 minutes. 4-Chlorobenzoyl chloride (a3) (18.4 g, 105 mmol) was added thereto, and the mixture was stirred for about 30 minutes. The reaction solution was slowly heated to room temperature, and then stirred for about 2 hours. The reaction solution was added with methanol, and then concentrated. The residue was purified by silica gel chromatography to obtain Intermediate a4 (13.1 g, yield 51%).

Synthesis of Intermediate a5

Intermediate a4 (12.0 g, 32.5 mmol) was added dropwise to tetrahydrofuran (200 mL). While stirring the resultant at about −78° C., methyllithium (32.5 mL, 32.5 mmol, 1.0 M ether solution) was added dropwise thereto, and the mixture was stirred for about 1 hour. The reaction solution was slowly heated to room temperature, and then stirred for about 6 hours. The reaction solution was added with methanol, and then concentrated. After dissolving the residue in toluene, the resultant was washed with water, and then dried over anhydrous magnesium sulfate and concentrated. The concentrated residue was dissolved in chloroform (300 mL). Methanesulfonic acid (10.0 g, 104 mmol) was added thereto, and the mixture was stirred and heated to reflux for about 6 hours. After the reaction solution was cooled to room temperature, it was washed with a saturated sodium hydrogen carbonate solution, and then dried over anhydrous magnesium sulfate and concentrated. The residue was purified by silica gel chromatography to obtain Intermediate a5 (7.52 g, yield 63%).

Synthesis of Intermediate a6

Intermediate a5 (5.50 g, 15.5 mmol) was added dropwise to chloroform (200 mL), and m-chloroperbenzoic acid (5.54 g, 22.5 mmol, 70%) was added thereto in five times. The reaction solution was slowly heated to room temperature, and then stirred at about 40° C. for about 6 hours. The resultant was washed with a saturated sodium hydrogen carbonate solution, and then dried over anhydrous magnesium sulfate and concentrated. The residue was dissolved in chloroform (300 mL). Methanesulfonic acid (7.20 g, 104 mmol) was added thereto, and the mixture was stirred and heated to reflux for about 6 hours. After the reaction solution was cooled to room temperature, it was washed with a saturated sodium hydrogen carbonate solution, and then dried over anhydrous magnesium sulfate and concentrated. The residue was purified by silica gel chromatography to obtain Intermediate a6 (3.01 g, yield 55%).

Synthesis of Compound 1

Under an argon atmosphere, Intermediate a6 (2.50 g, 9.57 mmol), bis(4-biphenyl)amine (3.38 g, 10.5 mmol), palladium bis(dibenzylidene acetone)(0) (165 mg, 0.287 mmol) and sodium tert-butoxide (2.76 g, 28.7 mmol) were added dropwise to a toluene suspension (200 mL). After adding tri(tert-butyl phosphine) (0.359 mL, 0.574 mmol, 1.6 M toluene solution), m-chloroperbenzoic acid (5.54 g, 22.5 mmol, 70%) was added thereto over five times at about 120° C. After the reaction solution was cooled slowly to room temperature, it was stirred for about 8 hours, and then filtered with Florisil® (or a suitable filter) and concentrated. The residue was purified by silica gel chromatography to obtain Compound 1 (4.48 g, yield 72%). The molecular weight of Compound 1 measured by FAB-MS was 649.

1-2. Synthesis of Compound 4

Compound 4, a monoamine compound according to an embodiment of the present disclosure, may be synthesized as shown in the following Reaction scheme 2, for example.

Reaction scheme 2

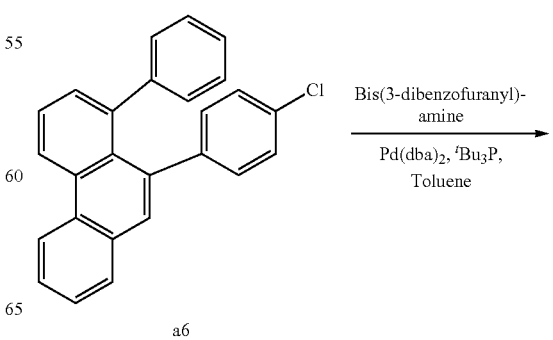

a6

33

-continued

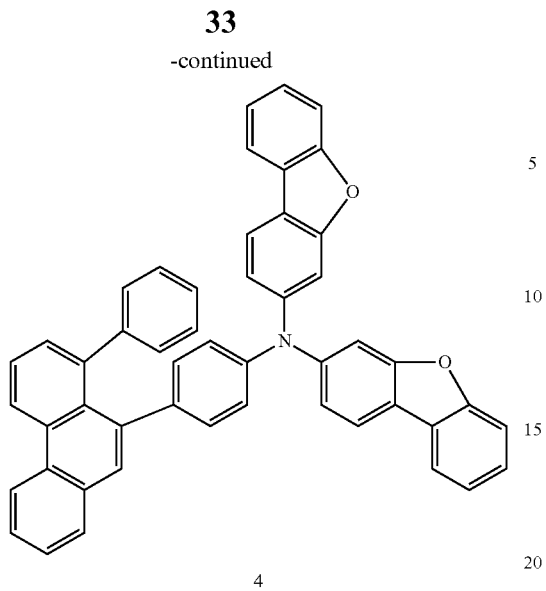

4

Synthesis of Compound 4

Compound 4 was obtained (yield 75%) by conducting the same synthetic method of Compound 1 except for utilizing bis(3-dibenzofuranyl)amine instead of bis(4-biphenyl)amine in Reaction scheme 1. The molecular weight of Compound 4 measured by FAB-MS was 677.

1-3. Synthesis of Compound 8

Compound 8, a monoamine compound according to an embodiment of the present disclosure, may be synthesized as shown in the following Reaction scheme 3, for example.

Reaction scheme 3

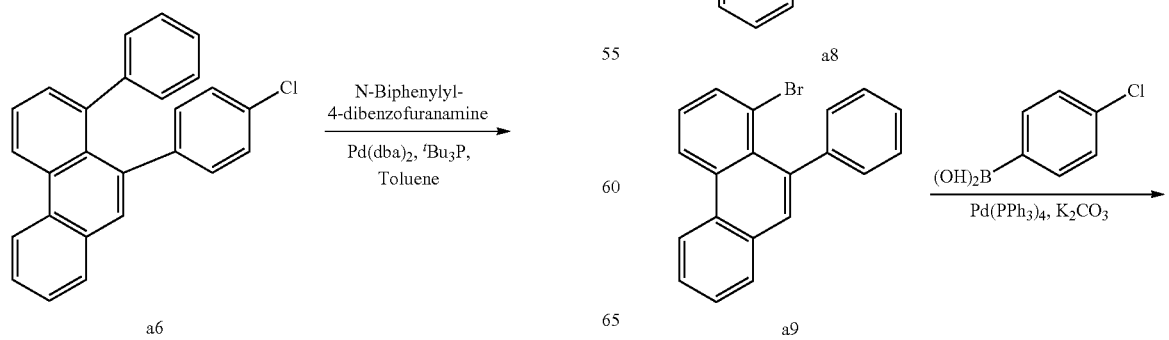

34

-continued

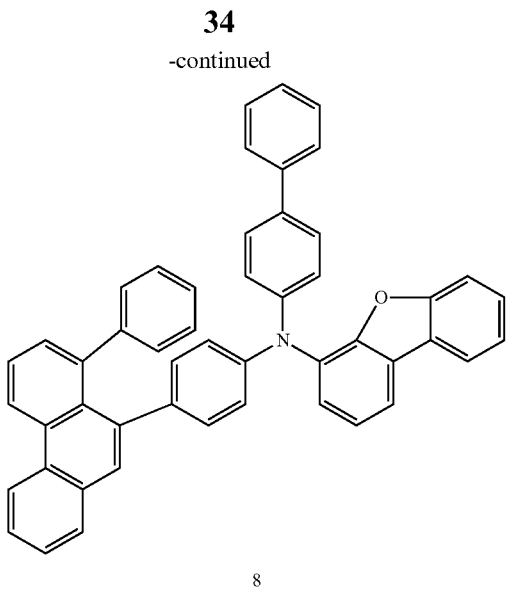

8

Synthesis of Compound 8

Compound 8 was synthesized (yield 72%) by conducting the same synthetic method of Compound 4 except for utilizing N-biphenylyl-4-dibenzofuranamine instead of bis(3-dibenzofuranyl)amine in Reaction scheme 2. The molecular weight of Compound 8 measured by FAB-MS was 663.

1-4. Synthesis of Compound 23

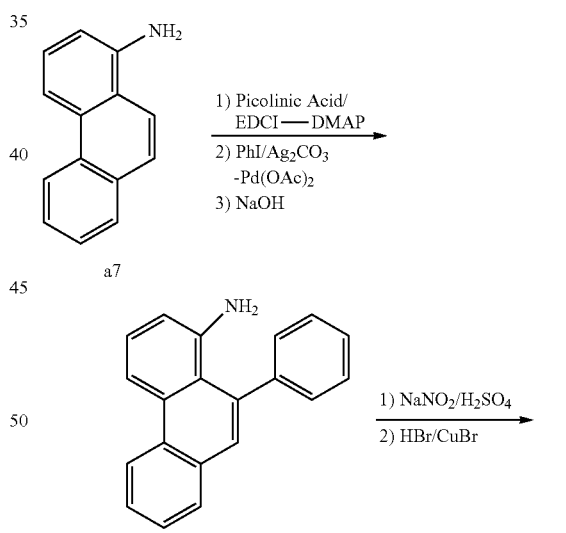

-continued

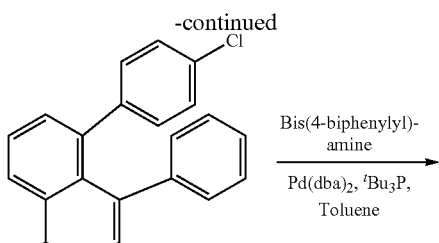

a10

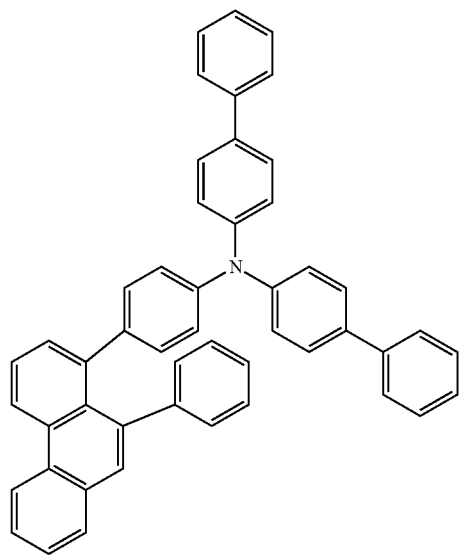

23

Synthesis of Intermediate a8

To a solution of 1-aminophenanthrene (a7) (7.73 g, 40.0 mmol), picolinic acid (5.42 g, 44.0 mmol) and DMAP (489 mg, 4.00 mmol) dissolved in anhydrous dichloromethane (100 mL), a solution of EDCl (9.43 g, 44.0 mmol) in anhydrous dichloromethane (50 mL) was added dropwise at about 0° C. After the reaction solution was stirred at room temperature for about 12 hours, it was added with water and then extracted with dichloromethane. An organic layer was dried over anhydrous magnesium sulfate and concentrated. The residue was purified by silica gel chromatography to obtain picolinate.

The picolinate thus obtained was mixed with iodobenzene (30.0 g, 147 mmol), silver acetate (8.73 g, 52.3 mmol) and palladium acetate (235 mg, 1.05 mmol), and the mixture was stirred at about 140° C. for about 24 hours. After the reaction solution was cooled to room temperature, it was diluted with dichloromethane, filtered on Celite® (or a diatomaceous earth based filter), and then concentrated. The residue was purified by silica gel chromatography to obtain a phenyl compound.

The phenyl compound thus obtained was added with NaOH (20 g) and 90% ethanol (160 mL), and the mixture was stirred and heated to reflux for about 24 hours. After the reaction solution was cooled to room temperature, it was extracted with dichloromethane. An organic layer was dried over anhydrous magnesium sulfate and concentrated. The residue was purified by silica gel chromatography to obtain Intermediate a8 (3.57 g, yield 38%).

Synthesis of Intermediate a9

To a mixture solution of sulfuric acid (98%, 14 mL) and water (100 mL) cooled to about 0° C., Intermediate a8 (3.30 g, 12.3 mmol) was added and an aqueous solution (20 mL) of sodium nitrite (1.01 g, 14.7 mmol) was added dropwise thereto under stirring. After the reaction solution was stirred for about 1 hour, it was added with copper (I) bromide (527 mg, 3.68 mmol) and hydrobromic acid (24%, 50 mL), and then stirred at about 0° C. for about 1 hour, at room temperature for about 2 hours, and additionally at about 70° C. for about 30 minutes. After the reaction solution was cooled to room temperature, it was extracted with toluene, filtered on Celite®, and then concentrated. The residue was purified by silica gel chromatography to obtain Intermediate a9 (2.65 g, yield 65%).

Synthesis of Intermediate a10

A mixture of Intermediate a9 (2.50 g, 7.50 mmol), 4-chlorophenylboronic acid (1.41 g, 9.00 mmol), tetrakis(triphenylphosphine) palladium (0) (260 mg, 0.225 mmol), potassium carbonate (5.18 g, 37.5 mmol), toluene (150 mL) and 66% ethanol (50 mL) was heated at about 90° C. for about 10 hours. After the reaction solution was cooled, it was filtered on Celite®, and extracted with toluene. An organic layer was dried over anhydrous magnesium sulfate and concentrated. The residue was purified by silica gel chromatography to obtain Intermediate a10 (2.00 g, yield 73%).

Synthesis of Compound 23

Compound 23 was synthesized (yield 70%) by conducting the same synthetic method of Compound 1 except for utilizing Intermediate a10 instead of Intermediate a6 in Reaction scheme 1. The molecular weight of Compound 23 measured by FAB-MS was 649.

2. Manufacturing of Organic Electroluminescence Devices Including Monoamine Compounds and Evaluation Thereof 2-1. Examples of Organic Electroluminescence Devices Including Monoamine Compounds Organic electroluminescence devices of Examples 1 to 4 and Comparative Examples 1 to 6 were manufactured by utilizing the Example Compounds 1, 4, 8 and 23 and Comparative Compounds C1 to C6 as a material for a hole transport layer, respectively.

Example Compounds

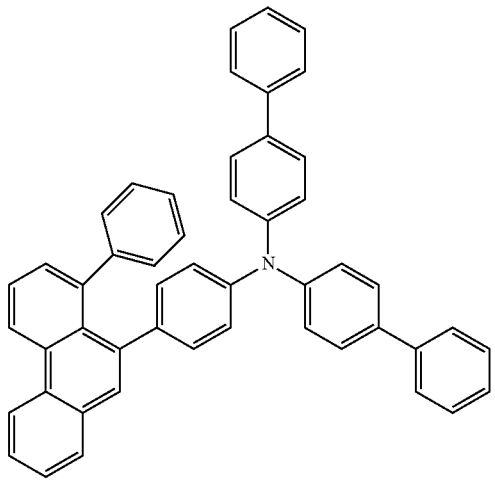

1

4
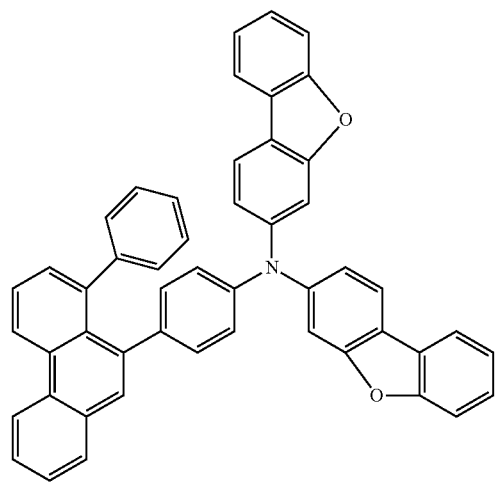
8
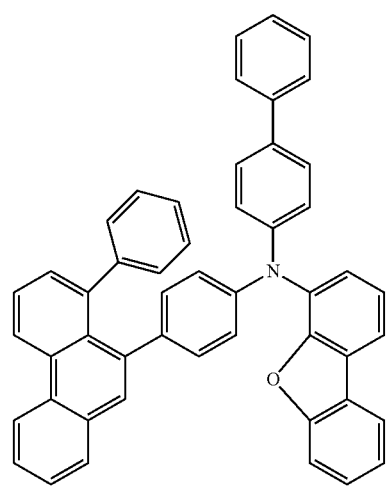
23
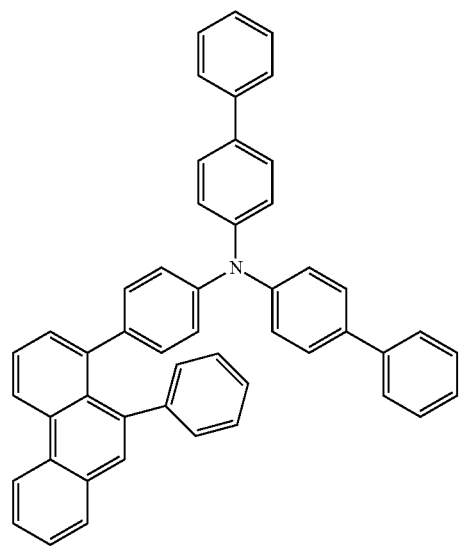
Comparative Compounds
C1
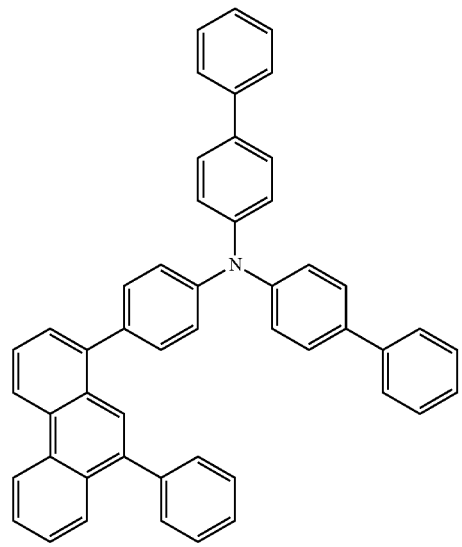
C2
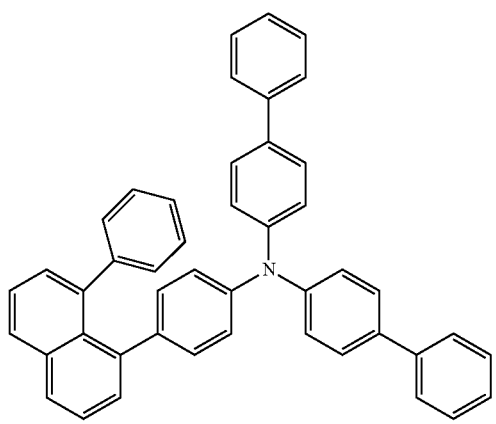
C3
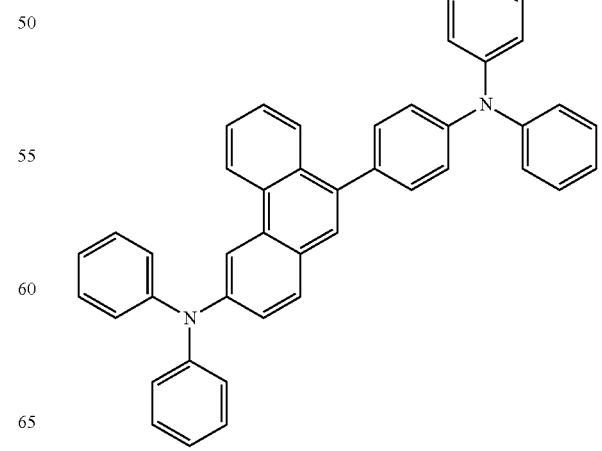

-continued

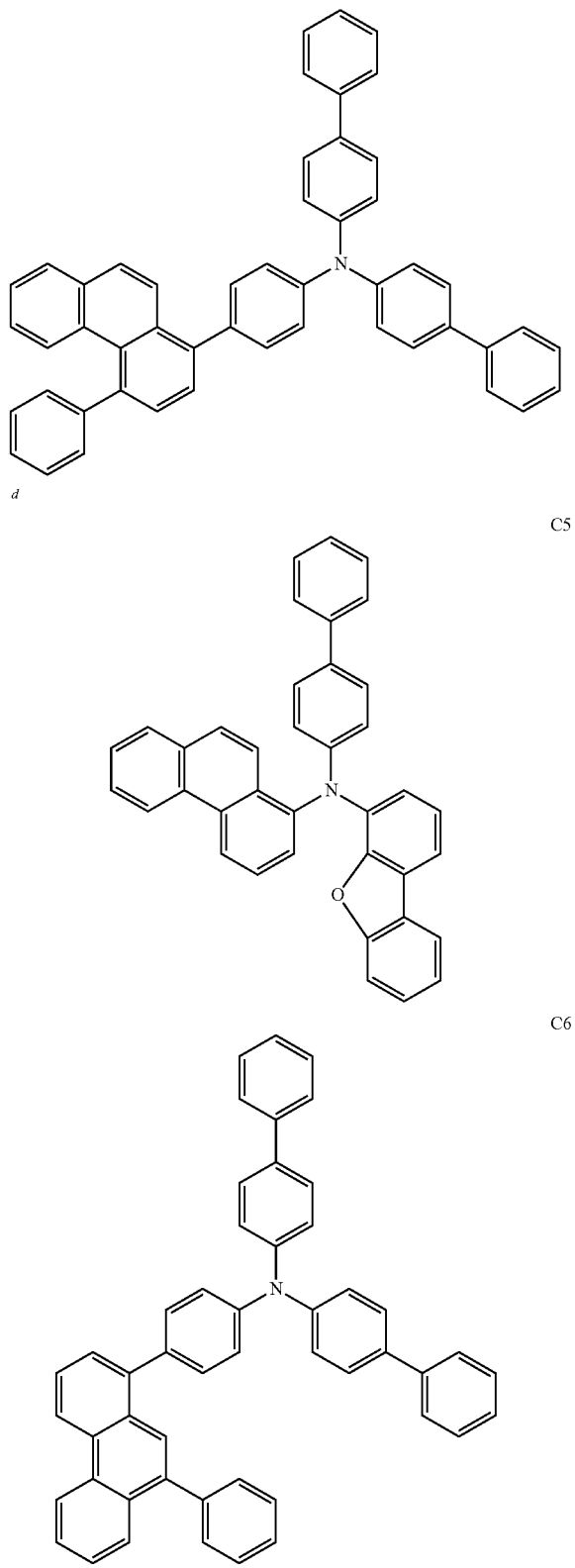

Manufacturing of Organic Electroluminescence Devices

The organic electroluminescence devices according to Examples 1 to 4 and Comparative Examples 1 to 6 were manufactured by forming a first electrode EL1 utilizing ITO to a thickness of about 150 nm, a hole injection layer HIL utilizing 2-TNATA to a thickness of about 60 nm, a hole transport layer HTL utilizing the example compounds or the comparative compounds to a thickness of about 30 nm, an emission layer EML utilizing ADN doped with 3% TBP to a thickness of about 25 nm, an electron transport layer ETL utilizing $Alq_3$ to a thickness of about 25 nm, an electron injection layer EIL utilizing LiF to a thickness of about 1 nm, and a second electrode EL2 utilizing Al to a thickness of about 100 nm. Each layer was formed by a vacuum deposition method.

Property Evaluation of Organic Electroluminescence Devices

The light emitting properties of organic electroluminescence devices were evaluated by utilizing a brightness light distribution characteristics measurement system C9920-11 (Hamamatsu Photonics, Japan). The device efficiency and device life were measured to evaluate the properties of the organic electroluminescence devices manufactured in Examples and Comparative Examples. The device efficiency was obtained at a current density of 10 $mA/cm^2$. The initial current density for the device life measurement was 1.0 $mA/cm^2$. The light emitting devices utilized in Examples and Comparative Examples are organic electroluminescence devices emitting blue light. The property evaluation results shown in Table 1 were based on the device efficiency and device life of the organic electroluminescence device according to Comparative Example 1 utilizing Comparative Compound C1 as a material for the hole transport layer (as a reference for 100% of the device efficiency and 100% for the device life).

TABLE 1

| Device manufacturing examples | HTL | Maximum light-emitting efficiency | Device life |
|---|---|---|---|
| Example 1 | Example Compound 1 | 106% | 120% |
| Example 2 | Example Compound 4 | 106% | 125% |
| Example 3 | Example Compound 8 | 111% | 112% |
| Example 4 | Example Compound 23 | 105% | 118% |
| Comparative Example 1 | Comparative Compound C1 | 100% | 100% |
| Comparative Example 2 | Comparative Compound C2 | 90% | 105% |
| Comparative Example 3 | Comparative Compound C3 | 57% | 88% |
| Comparative Example 4 | Comparative Compound C4 | 84% | 91% |
| Comparative Example 5 | Comparative Compound C5 | 95% | 83% |
| Comparative Example 6 | Comparative Compound C6 | 95% | 97% |

Referring to the results in Table 1, it may be found that the organic electroluminescence devices utilizing the monoamine compounds according to an embodiment of the present disclosure as a material for a hole transport layer achieve high efficiency and a long device life.

For example, it may be found that the organic electroluminescence devices of Examples 1 to 4 attain high efficiency and long life when compared with those of Comparative Examples 1 to 6. The organic electroluminescence devices of Examples 1 to 4 have device efficiency of 105% to 111% and device life of 112% to 125%, thereby attaining a long device life. In addition, the organic electroluminescence devices of Comparative Examples 1 to 6 have device efficiency of 57% to 100% and device life of 83% to 105%, which shows a shorter device life when compared with those of Examples.

In order to explain the difference in the conformation of the compounds utilized in Examples and Comparative Examples, their positions of substituents are defined based on (e.g., with reference to) the arylamine group -(L)N(Ar$_1$) (Ar$_2$) as shown in Scheme A and Scheme B below.

In the compounds utilized in Examples 1 to 4, the arylamine group and Ar$_3$ are substituted at positions as shown in Scheme A or Scheme B below, which are different from those of Comparative Examples.

Scheme A

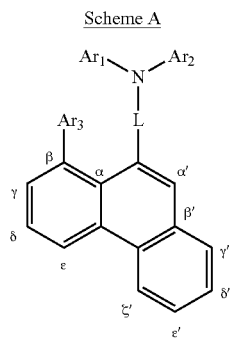

Scheme B

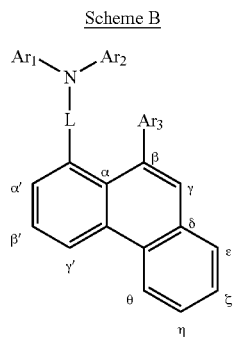

For example, in the compounds utilized in Examples 1 to 4 having the conformation of Scheme A or Scheme B, Ar$_3$ is substituted at the carbon atom at β-position against the diarylamine group.

Because the diarylamine group and Ar$_3$ in Scheme A and Scheme B are combined with SP$^2$ hybrid orbital of the carbon atom forming the phenanthryl core, the diarylamine group and Ar$_3$ may be positioned in a substantially parallel manner to each other. Although the steric hindrance between the diarylamine group and Ar$_3$ causes a repulsive force to modify the bond angle a little, the diarylamine group and Ar$_3$ of the compounds utilized in Examples 1 to 4 may be positioned close to being parallel to each other (e.g., substantially parallel to each other) when compared with those of Comparative Examples. Accordingly, it appears that the stereochemical interaction derived from the above-described specific positions of substituents leads to high efficiency and long life of the device utilizing the compounds.

In addition, in Comparative Compounds C1 and C6 utilized in Comparative Examples 1 and 6, the substituents corresponding to Ar$_3$ of the Example Compounds are substituted at positions α' and γ, respectively. That is, in Comparative Compound C1 and C6 having the conformation different from those of Scheme A and Scheme B, the diarylamine group and the substituents corresponding to Ar$_3$ are not positioned in a parallel manner to each other. Accordingly, it appears that Comparative Compounds C1 and C6 do not have such stereochemical interaction as the monoamine compound according to an embodiment of the present disclosure, thereby failing to accomplish high efficiency and long life for the device utilizing the compounds. Comparative Compound C2 utilized in Comparative Example 2 has a naphthyl group, which is different from the phenanthryl group of the Example Compounds, and has a conformation different from those of Example Compounds. Accordingly, Example Compounds have physical or chemical characteristics different from those of Comparative Compound C2, which appears to result in high efficiency and long life of the device utilizing the compounds. For example, device efficiency is significantly (e.g., remarkably) enhanced in the organic electroluminescence device utilizing Example Compounds.

Comparative Compound C3 utilized in Comparative Example 3 is a diamine compound, which is different from the monoamine compounds, and has a substituent at a position different from the monoamine compounds according to an embodiment of the present disclosure. In Comparative Compound C4 utilized in Comparative Example 4, the substituent corresponding to Ar$_3$ of the Example Compounds is substituted at the γ' position, which is different from Scheme A and Scheme B. Comparative Compound C5 utilized in Comparative Example 5 has no substituent corresponding to Ar$_3$ of the monoamine compounds according to an embodiment of the present disclosure. Accordingly, Example Compounds have physical or chemical characteristics different from those of Comparative Compounds C3 to C5, which appears to result in high efficiency and long life of the device utilizing the compounds.

In conclusion, the monoamine compounds according to an embodiment of the present disclosure have a stereochemical effect resulting from the characteristic interaction due to the conformation and positions of the substituents, which appears to attain the above-described high efficiency and long life of the device utilizing the compounds.

The organic electroluminescence device according to an embodiment of the present disclosure may attain high efficiency and a long device life.

The monoamine compound according to an embodiment of the present disclosure may be applied to an organic electroluminescence device, thereby contributing to high efficiency and a long device life.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed. Furthermore, the scope of the present disclosure is to be determined by the broadest permissible interpretation of the following claims and their equivalents, and shall not be restricted or limited by the foregoing detailed description.

What is claimed is:

1. An organic electroluminescence device, comprising:
a first electrode;
a second electrode on the first electrode; and
a plurality of organic layers between the first electrode and the second electrode,
wherein at least one of the plurality of organic layers comprises a monoamine compound represented by the following Formula 1:

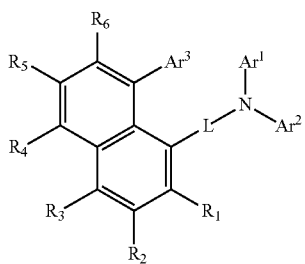

Formula 1 wherein in Formula 1,
L is a direct linkage, a substituted or unsubstituted arylene group having 6 to 30 carbon atoms for forming a ring, or a substituted or unsubstituted heteroarylene group having 2 to 30 carbon atoms for forming a ring,
$Ar_1$ and $Ar_2$ are each independently a substituted or unsubstituted aryl group having 6 to 30 carbon atoms for forming a ring, or a substituted or unsubstituted heteroaryl group having 2 to 30 carbon atoms for forming a ring,
$Ar_3$ is a substituted or unsubstituted aryl group having 6 to 30 carbon atoms for forming a ring, or a substituted or unsubstituted heteroaryl group having 2 to 30 carbon atoms for forming a ring,
$R_1$ to $R_6$ are each independently a hydrogen atom, a deuterium atom, a halogen atom, a cyano group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted alkoxy group having 1 to 20 carbon atoms, a substituted or unsubstituted alkylthio group having 1 to 20 carbon atoms, or a substituted or unsubstituted silyl group having 1 to 40 carbon atoms, and
one pair of $R_2$ and $R_3$, or $R_4$ and $R_5$ combine with each other to form a substituted or unsubstituted benzene ring.

2. The organic electroluminescence device of claim 1, wherein L is a substituted or unsubstituted phenylene group, a substituted or unsubstituted divalent biphenyl group, or a substituted or unsubstituted dibenzofuranylene group.

3. The organic electroluminescence device of claim 1, wherein $Ar_1$ and $Ar_2$ are each independently a substituted or unsubstituted phenyl group, a substituted or unsubstituted biphenyl group, a substituted or unsubstituted fluorenyl group, a substituted or unsubstituted dibenzofuranyl group, or a substituted or unsubstituted dibenzothiophenyl group.

4. The organic electroluminescence device of claim 1, wherein $Ar_1$ and $Ar_2$ are each independently an aryl group having 6 to 30 carbon atoms for forming a ring substituted with a phenyl group or a naphthyl group.

5. The organic electroluminescence device of claim 1, wherein $Ar_3$ is a substituted or unsubstituted phenyl group, a substituted or unsubstituted biphenyl group, or a substituted or unsubstituted naphthyl group.

6. The organic electroluminescence device of claim 1, wherein the monoamine compound represented by Formula 1 is represented by the following Formula 2-1 or 2-2:

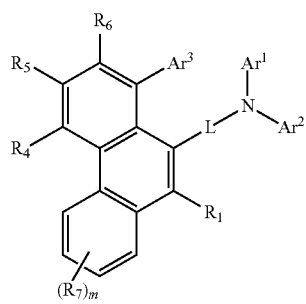

Formula 2-1

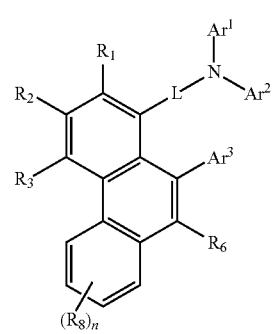

Formula 2-2 wherein in Formulae 2-1 and 2-2,
$R_7$ and $R_8$ are each independently a hydrogen atom, a deuterium atom, a halogen atom, a cyano group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted alkoxy group having 1 to 20 carbon atoms, a substituted or unsubstituted alkylthio group having 1 to 20 carbon atoms, or a substituted or unsubstituted silyl group having 1 to 40 carbon atoms, m and n are each independently an integer of 0 to 4, and L, $Ar_1$ to $Ar_3$, and $R_1$ to $R_6$ are the same as respectively defined with respect to Formula 1.

7. The organic electroluminescence device of claim 1, wherein the monoamine compound represented by Formula 1 is represented by the following Formula 3:

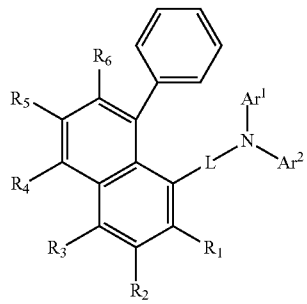

Formula 3 wherein in Formula 3, L, $Ar_1$, $Ar_2$, and $R_1$ to $R_6$ are the same as respectively defined with respect to Formula 1.

8. The organic electroluminescence device of claim 1, wherein the monoamine compound represented by Formula 1 is represented by the following Formula 4:

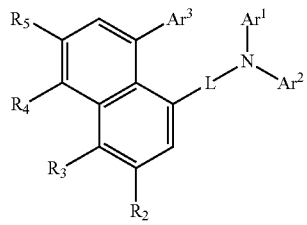

Formula 4 wherein in Formula 4, another pair of $R_2$ and $R_3$, or $R_4$ and $R_5$, which do not form the substituted or unsubstituted benzene ring, are each a hydrogen atom, and L and $Ar_1$ to $Ar_3$ are the same as respectively defined with respect to Formula 1.

9. The organic electroluminescence device of claim 1, wherein the plurality of organic layers comprises:

a hole transport region on the first electrode;

an emission layer on the hole transport region; and an electron transport region on the emission layer, and the hole transport region comprises the monoamine compound represented by Formula 1.

10. The organic electroluminescence device of claim 9, wherein the emission layer is to emit blue light with a wavelength range of about 440 nm to about 490 nm.

11. The organic electroluminescence device of claim 1, wherein the monoamine compound represented by Formula 1 comprises at least one selected from the group consisting of compounds represented in the following Compound Group 1:

[Compound Group 1]

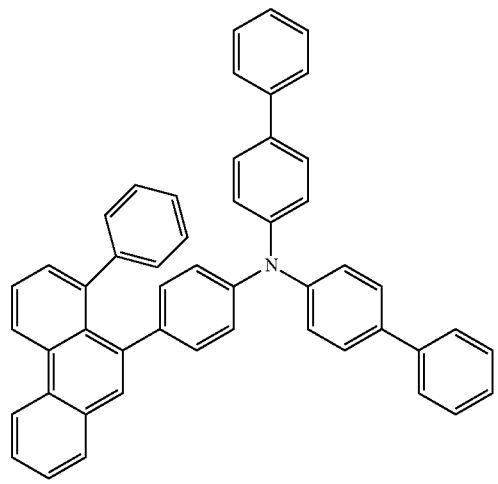

1

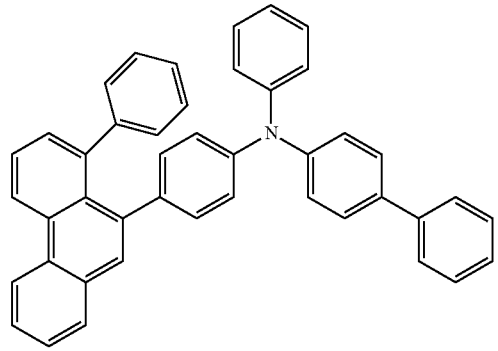

2

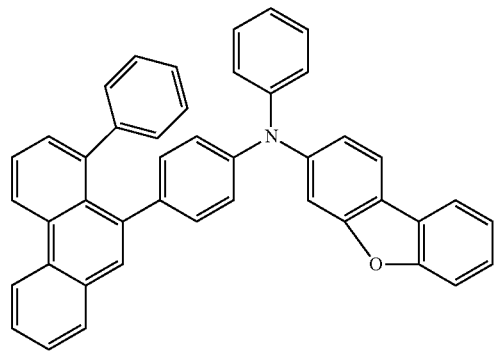

3

4
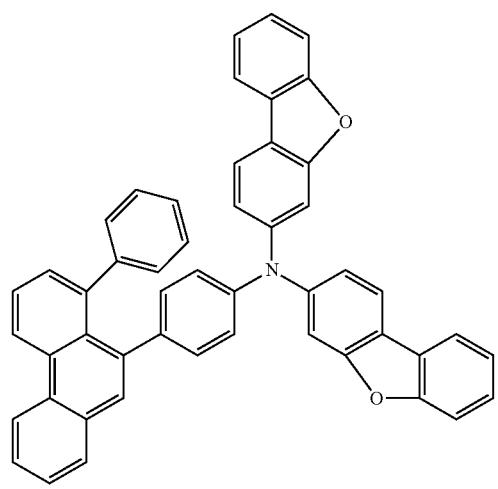
5
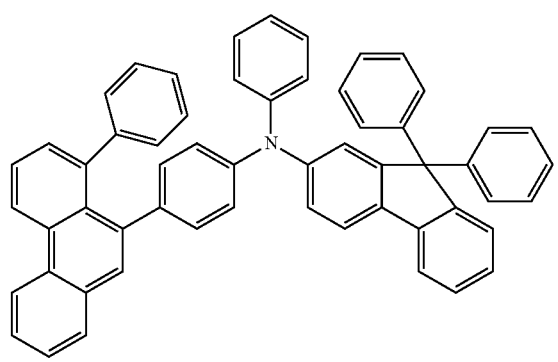
6
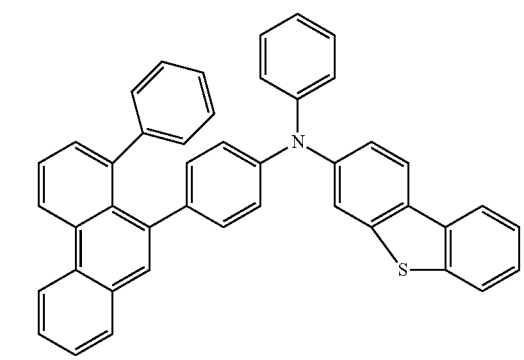
7
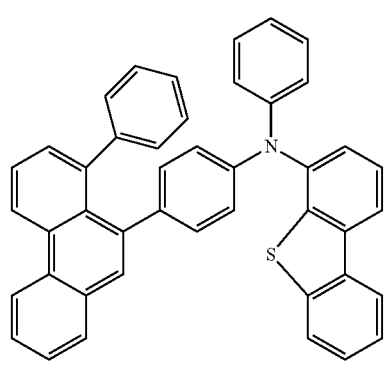
8
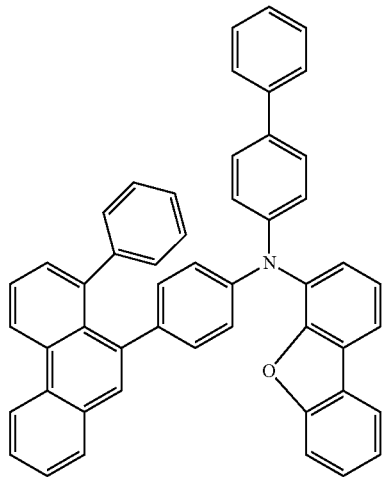
9
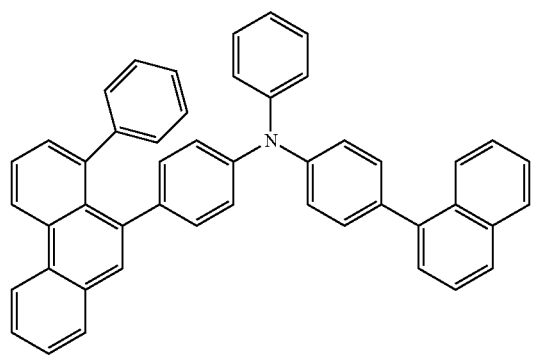

11
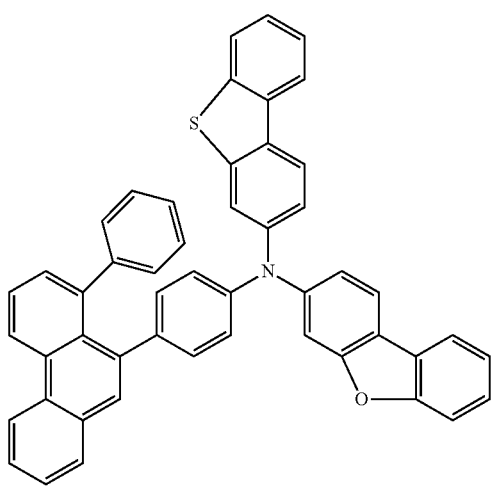
12
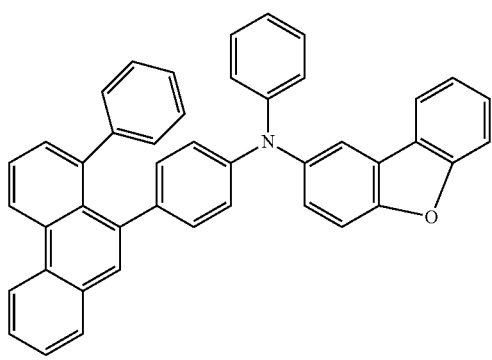
13
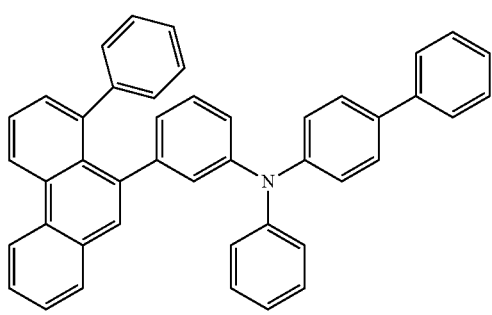
14
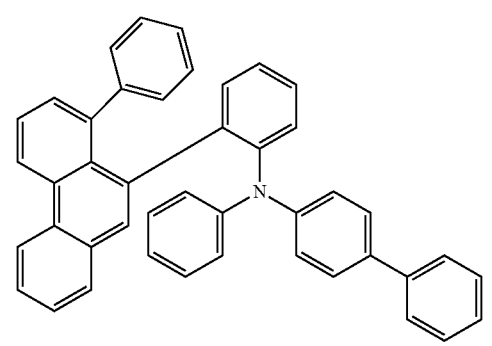
15
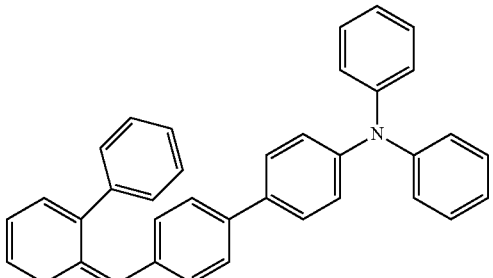
16
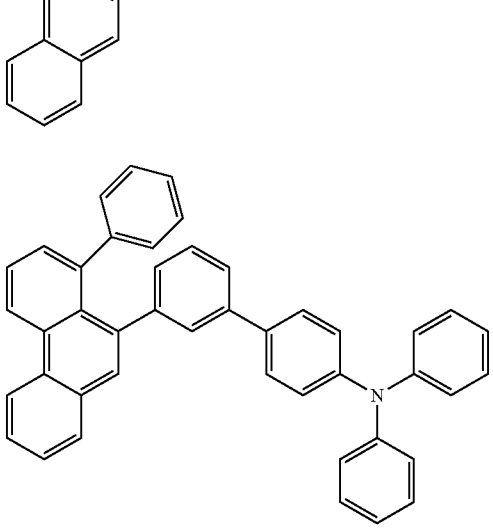
17
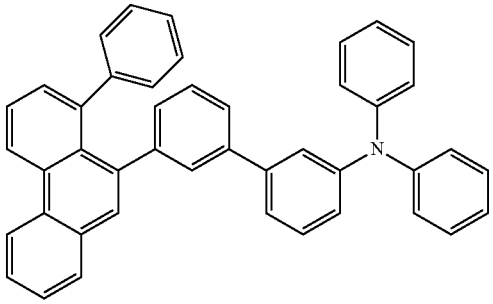
18
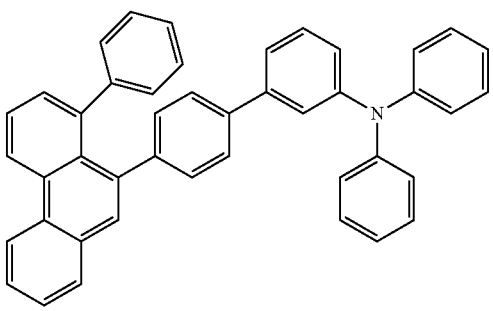

19
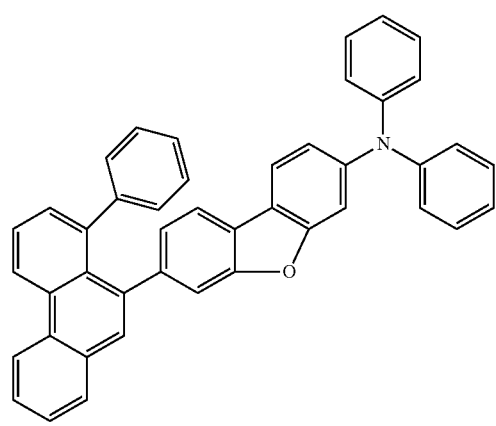
20
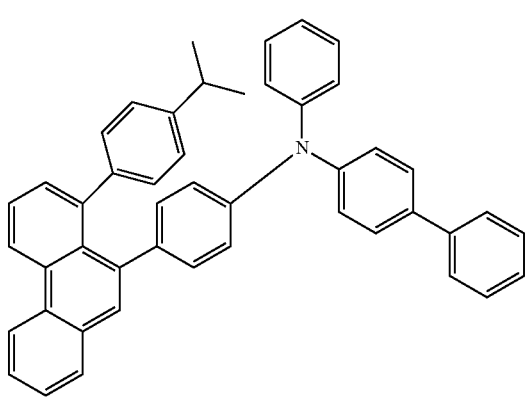
21
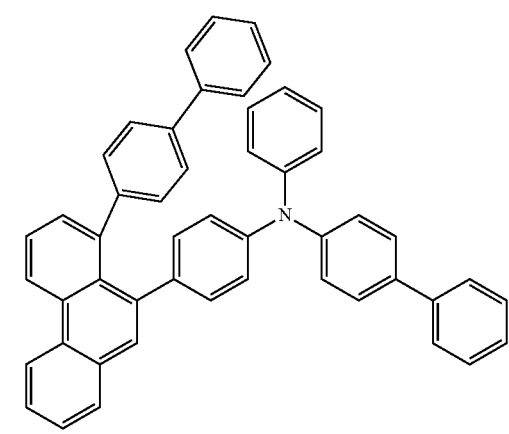
22
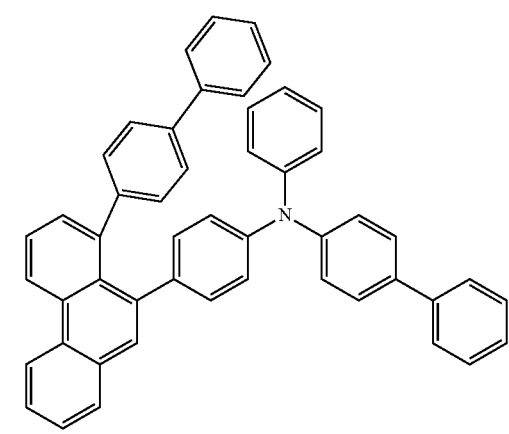
23
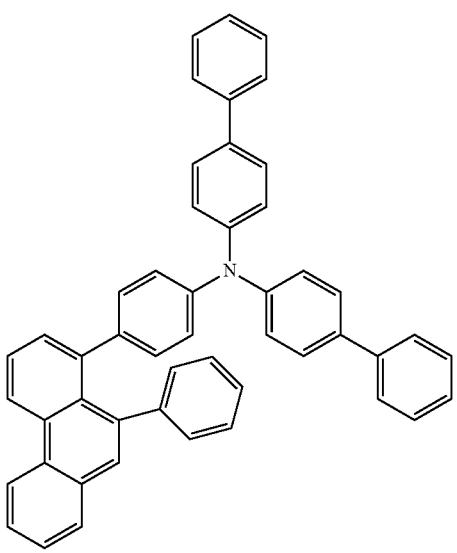
24
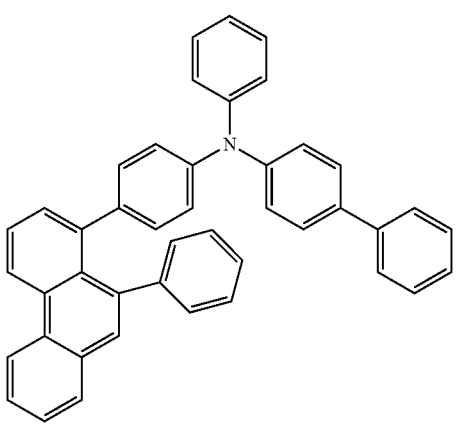
25
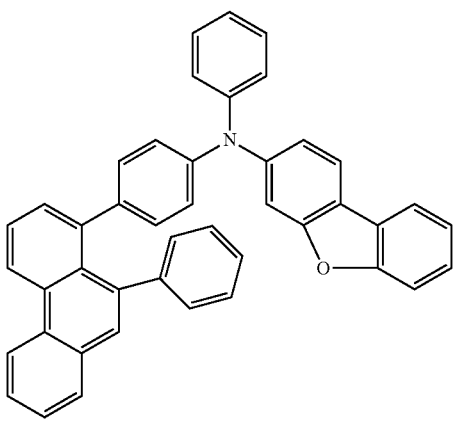

26
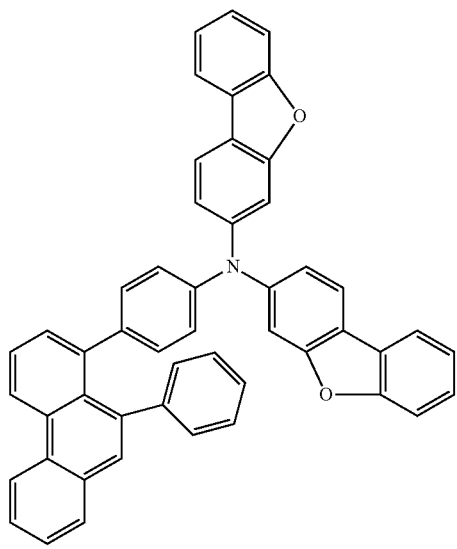
27
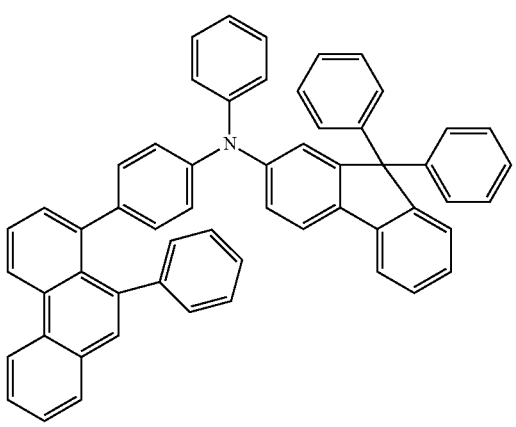
28
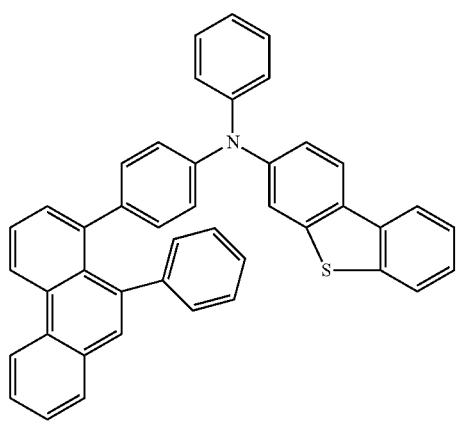
29
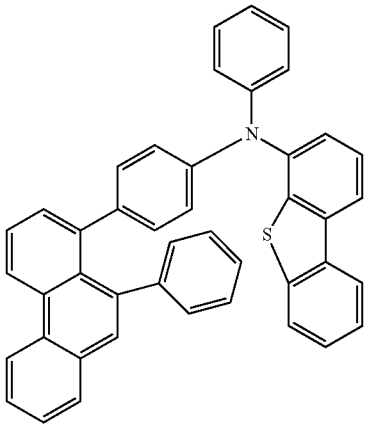
30
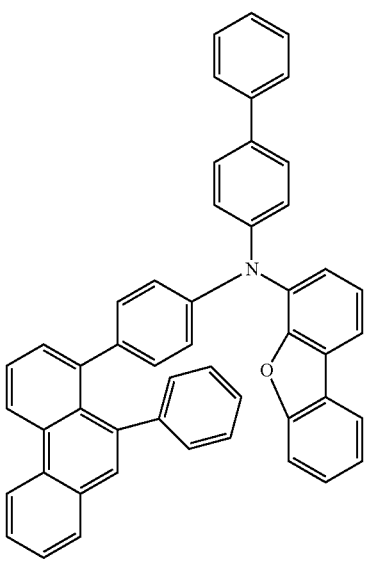
31
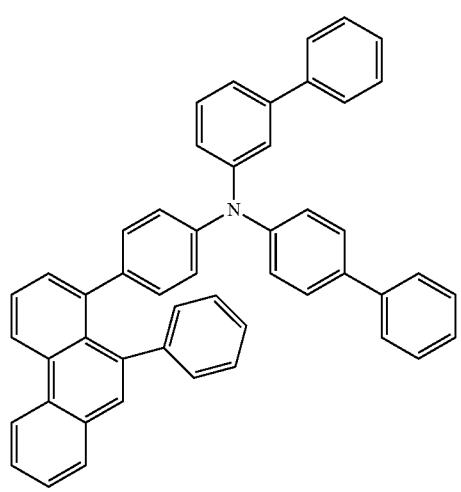

32
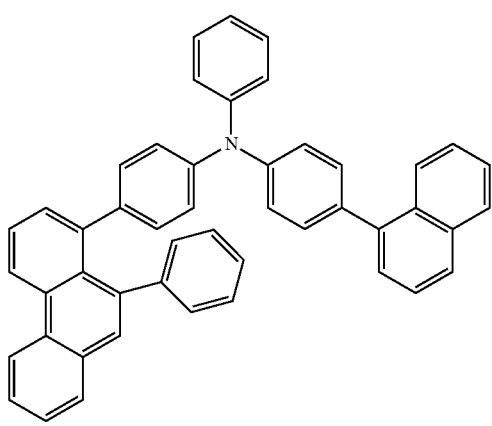
33
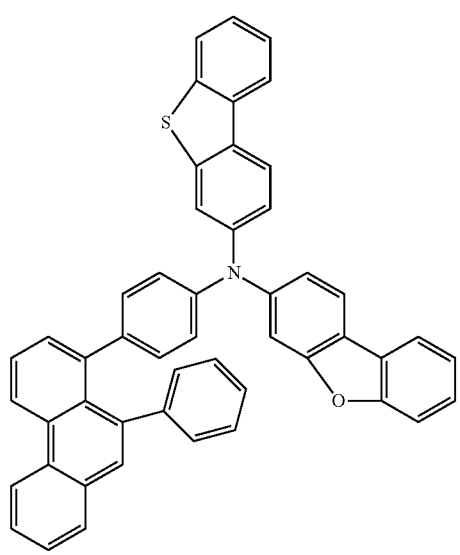
34
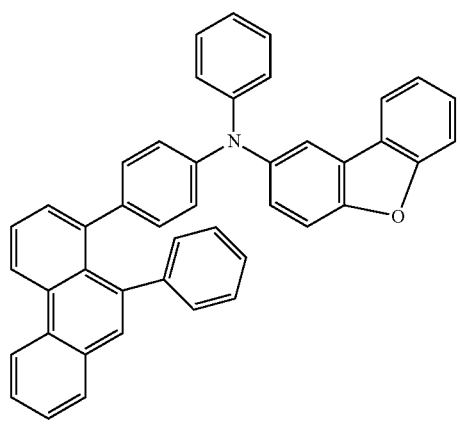
35
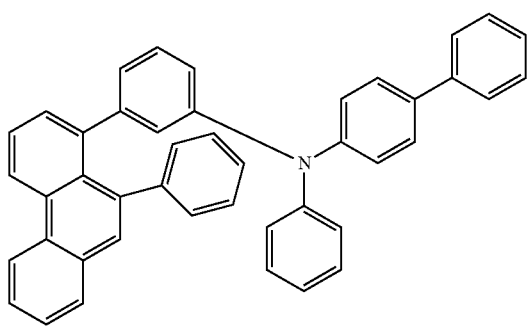
36
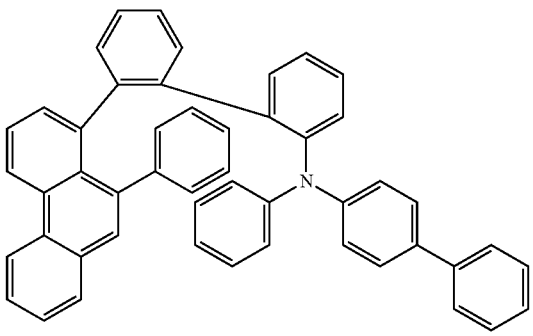
37
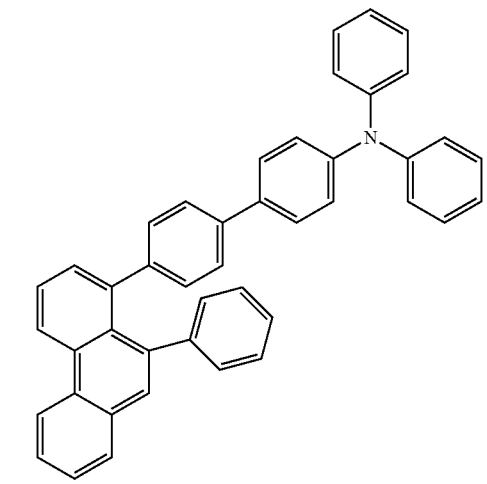
38
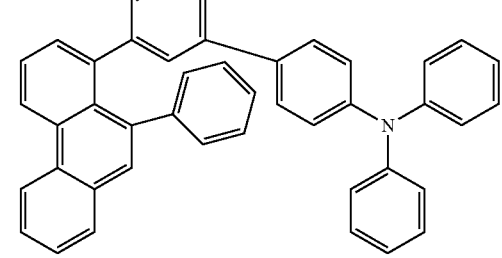

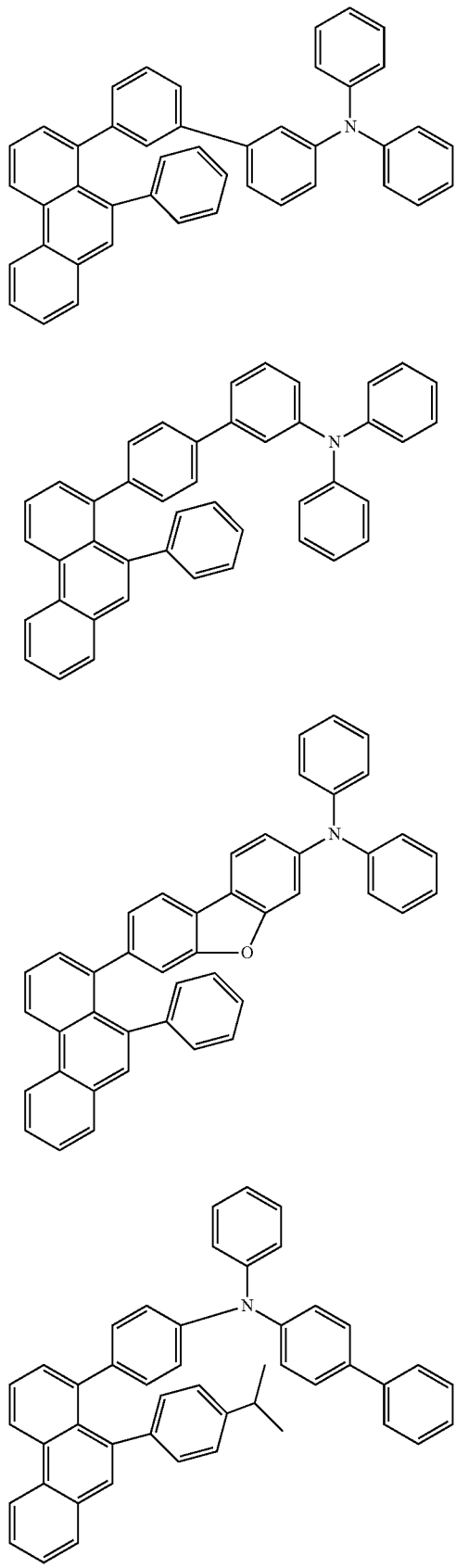

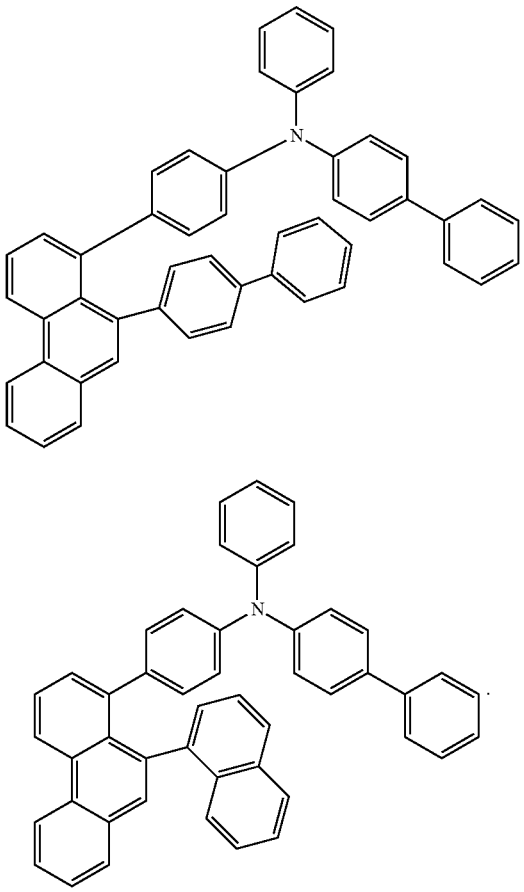

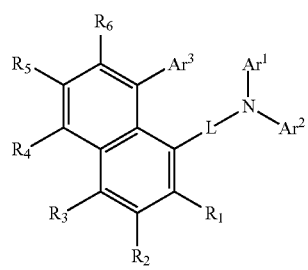

12. A monoamine compound represented by the following Formula 1:

Formula 1 wherein in Formula 1,

L is a direct linkage, a substituted or unsubstituted arylene group having 6 to 30 carbon atoms for forming a ring, or a substituted or unsubstituted heteroarylene group having 2 to 30 carbon atoms for forming a ring, $Ar_1$ and $Ar_2$ are each independently a substituted or unsubstituted aryl group having 6 to 30 carbon atoms for forming a ring, or a substituted or unsubstituted heteroaryl group having 2 to 30 carbon atoms for forming a ring, $Ar_3$ is a substituted or unsubstituted aryl group having 6 to 30 carbon atoms for forming a ring, or a substituted or unsubstituted heteroaryl group having 2 to 30 carbon atoms for forming a ring, R₁ to R₆ are each independently a hydrogen atom, a deuterium atom, a halogen atom, a cyano group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted alkoxy group having 1 to 20 carbon atoms, a substituted or unsubstituted alkylthio group having 1 to 20 carbon atoms, or a substituted or unsubstituted silyl group having 1 to 40 carbon atoms, and one pair of R₂ and R₃, or R₄ and R₅ combine with each other to form a substituted or unsubstituted benzene ring.

13. The monoamine compound of claim 12, wherein L is a substituted or unsubstituted phenylene group, a substituted or unsubstituted divalent biphenyl group, or a substituted or unsubstituted dibenzofuranylene group.

14. The monoamine compound of claim 12, wherein Ar₁ and Ar₂ are each independently a substituted or unsubstituted phenyl group, a substituted or unsubstituted biphenyl group, a substituted or unsubstituted fluorenyl group, a substituted or unsubstituted dibenzofuranyl group, or a substituted or unsubstituted dibenzothiophenyl group.

15. The monoamine compound of claim 12, wherein Ar₁ and Ar₂ are each independently an aryl group having 6 to 30 carbon atoms for forming a ring substituted with a phenyl group or a naphthyl group.

16. The monoamine compound of claim 12, wherein Ar₃ is a substituted or unsubstituted phenyl group, a substituted or unsubstituted biphenyl group, or a substituted or unsubstituted naphthyl group.

17. The monoamine compound of claim 12, wherein the monoamine compound represented by Formula 1 is represented by the following Formula 2-1 or 2-2:

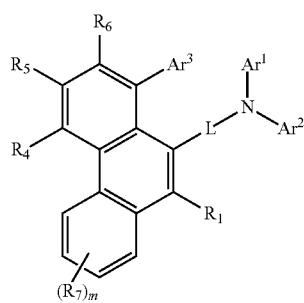

Formula 2-1

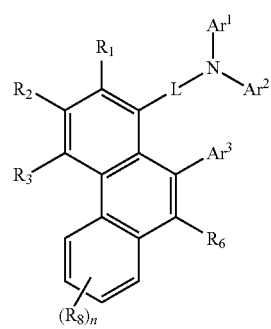

Formula 2-2 wherein in Formulae 2-1 and 2-2,

R₇ and R₈ are each independently a hydrogen atom, a deuterium atom, a halogen atom, a cyano group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted alkoxy group having 1 to 20 carbon atoms, a substituted or unsubstituted alkylthio group having 1 to 20 carbon atoms, or a substituted or unsubstituted silyl group having 1 to 40 carbon atoms, m and n are each independently an integer of 0 to 4, and L, Ar₁ to Ar₃, and R₁ to R₆ are the same as respectively defined with respect to Formula 1.

18. The monoamine compound of claim 12, wherein the monoamine compound represented by Formula 1 is represented by the following Formula 3:

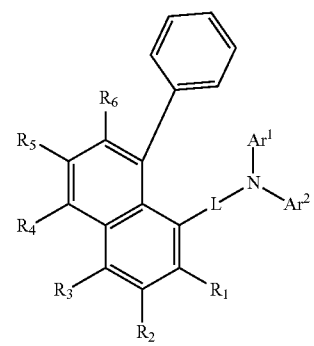

Formula 3 wherein in Formula 3, L, Ar₁, Ar₂, and R₁ to R₆ are the same as respectively defined with respect to Formula 1.

19. The monoamine compound of claim 12, wherein the monoamine compound represented by Formula 1 is represented by the following Formula 4:

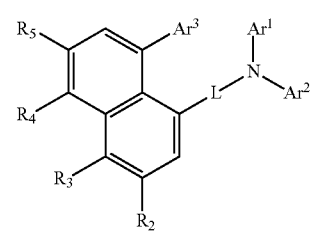

Formula 4 wherein Formula 4, another pair of R₂ and R₃, or R₄ and R₅, which do not form the substituted or unsubstituted benzene ring, are each a hydrogen atom, and L, and Ar₁ to Ar₃ are the same as respectively defined with respect to Formula 1.

20. The monoamine compound of claim 12, wherein the monoamine compound represented by Formula 1 is represented by any one of compounds represented in the following Compound Group 1:
[Compound Group 1]
1
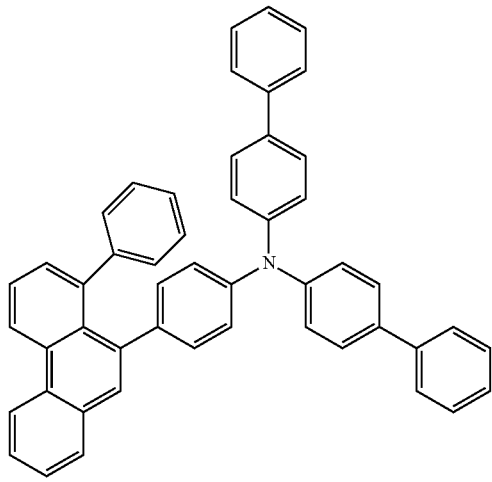
2
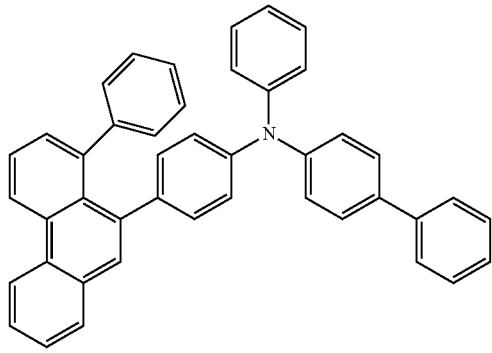
3
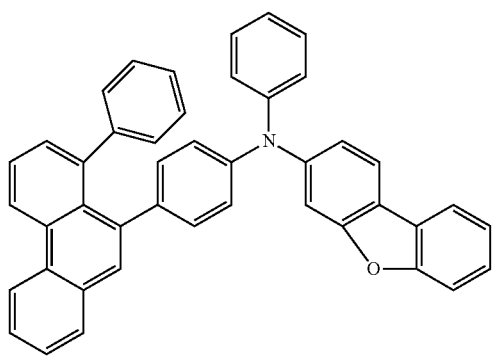
4
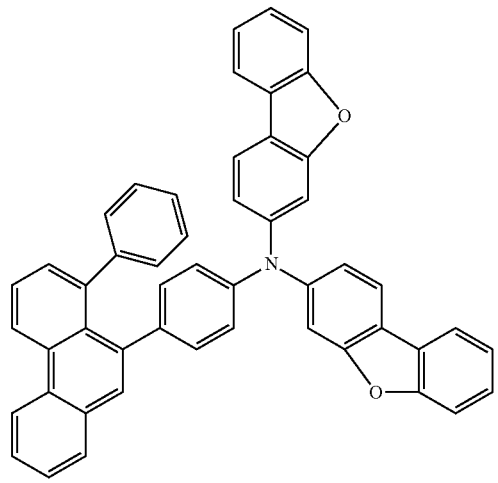
5
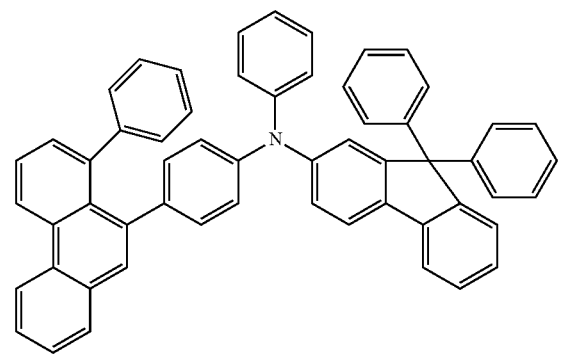
6
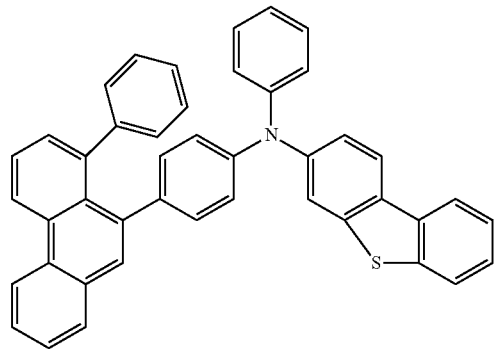
7
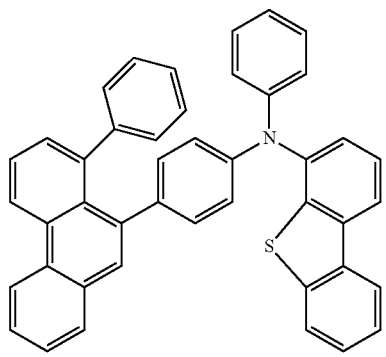

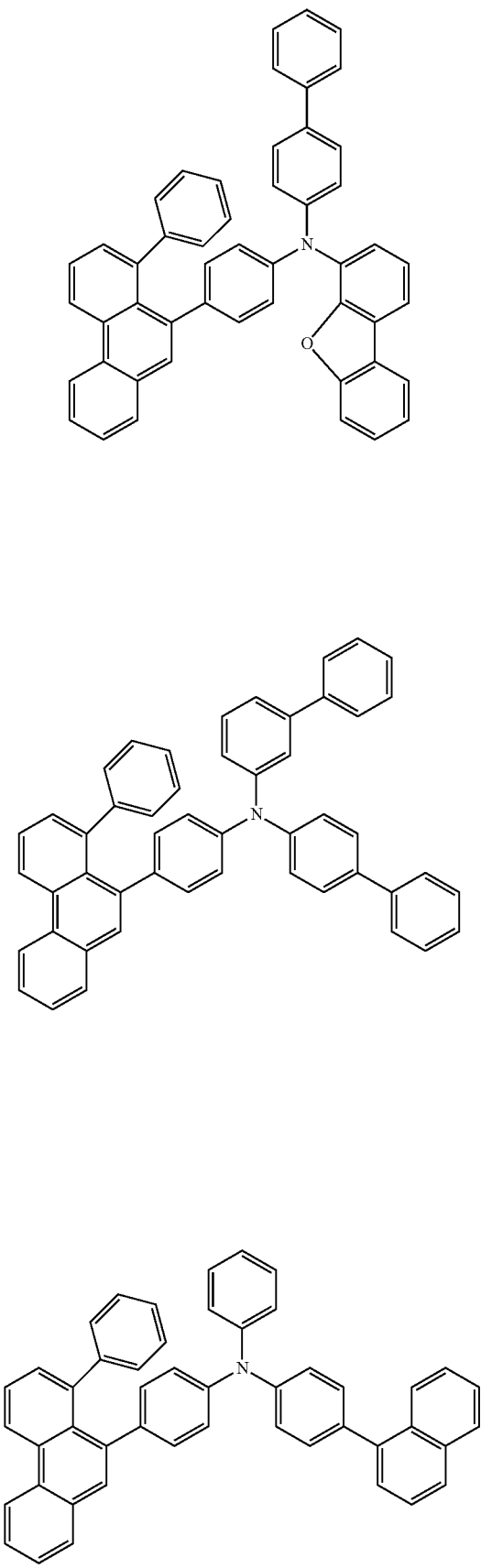
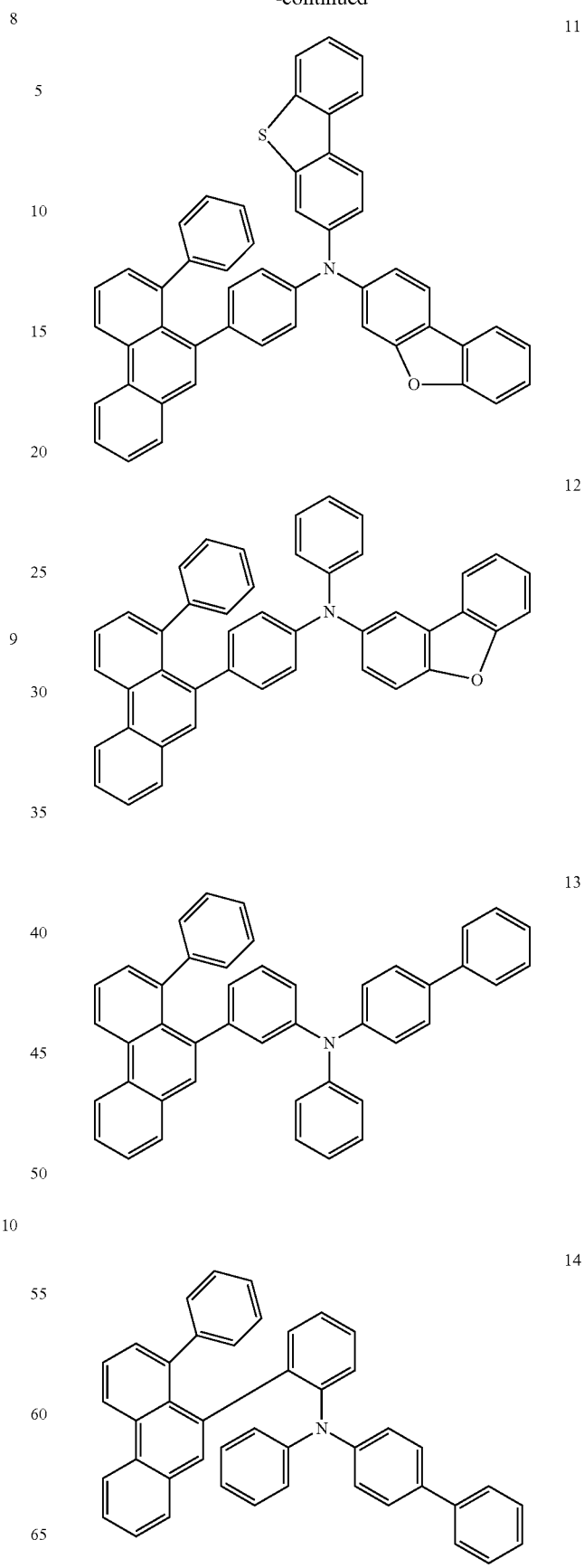

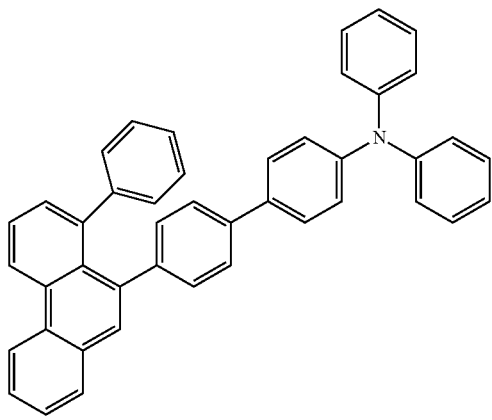
15
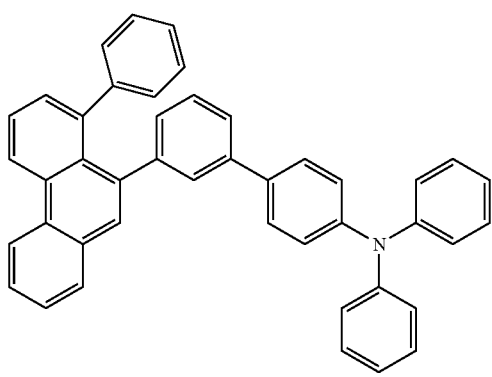
16
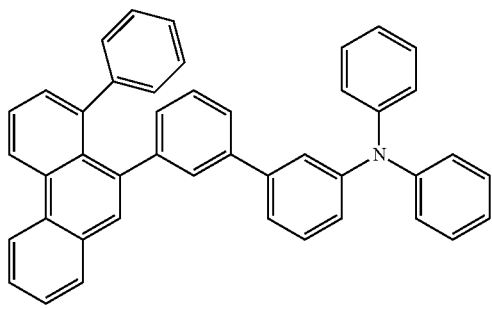
17
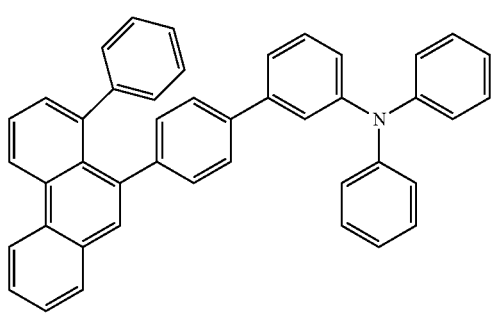
18
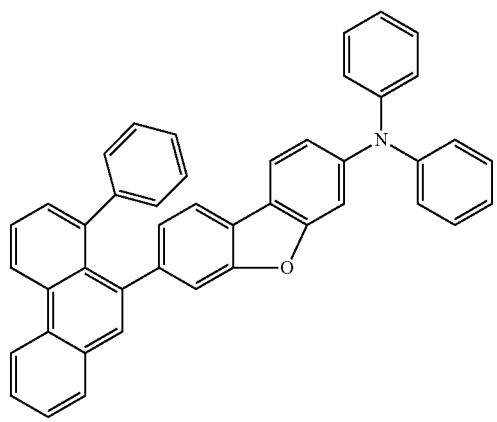
19
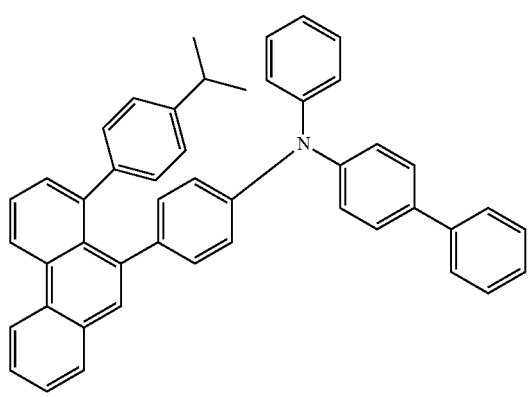
20
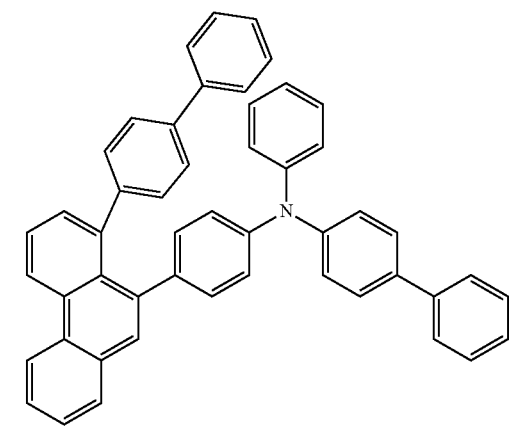
21
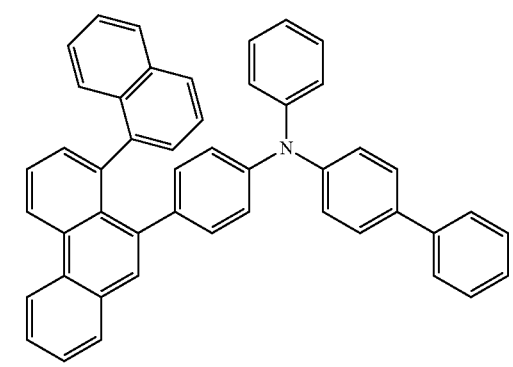
22

23
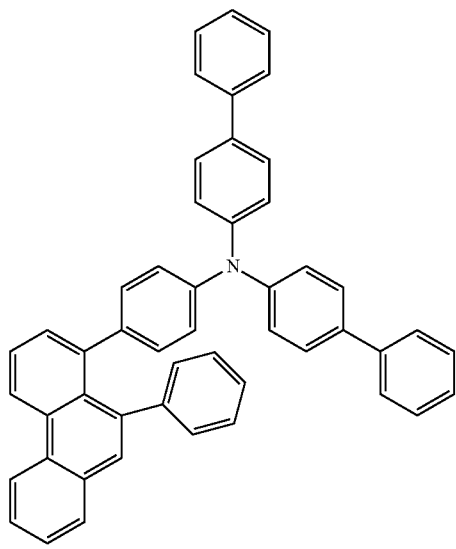
24
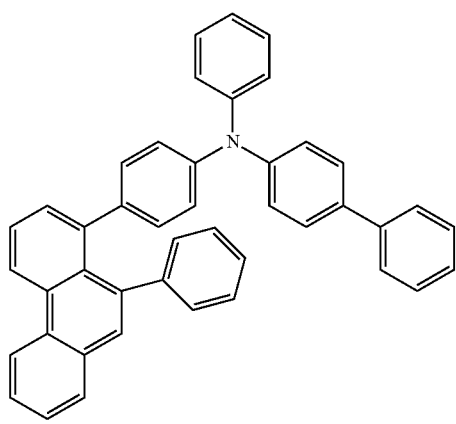
25
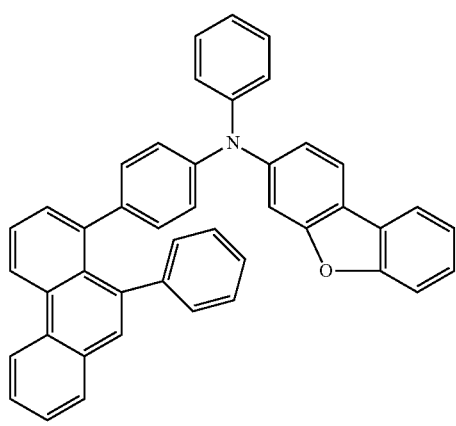
26
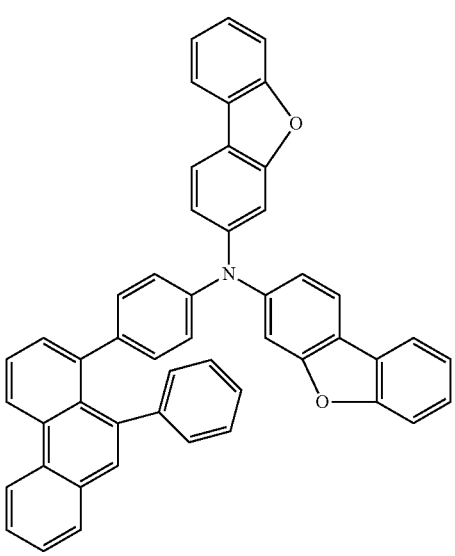
27
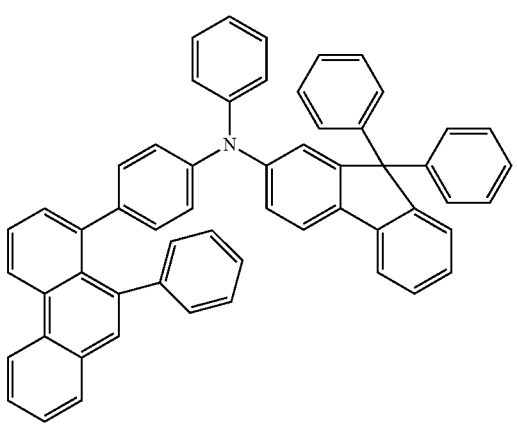
28
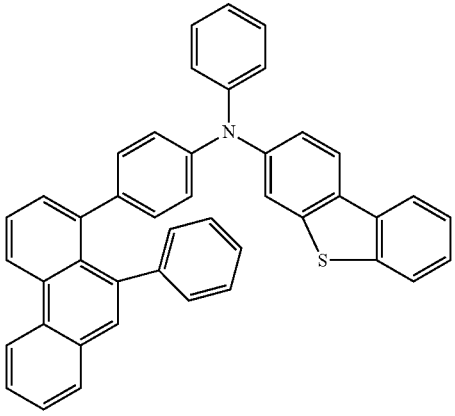

29
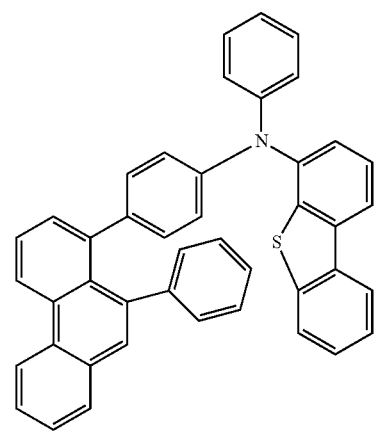
30
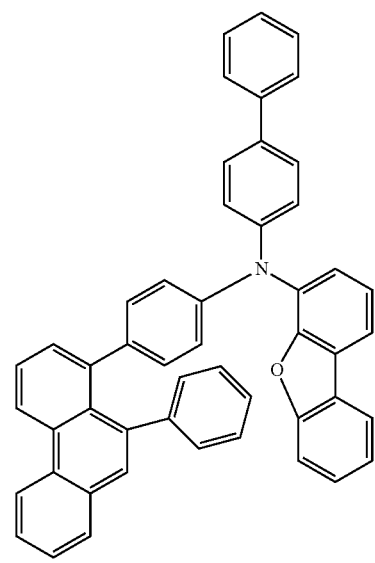
31
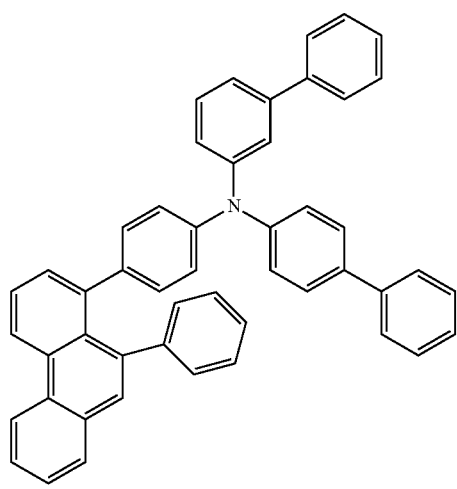
32
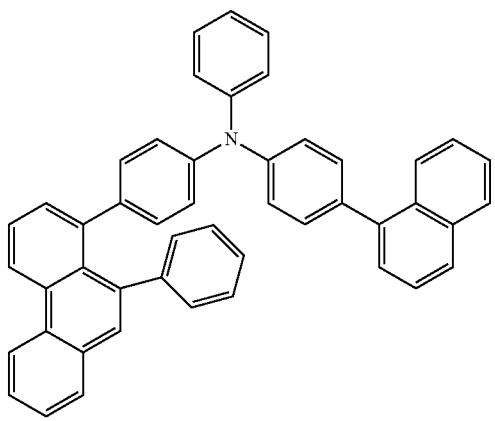
33
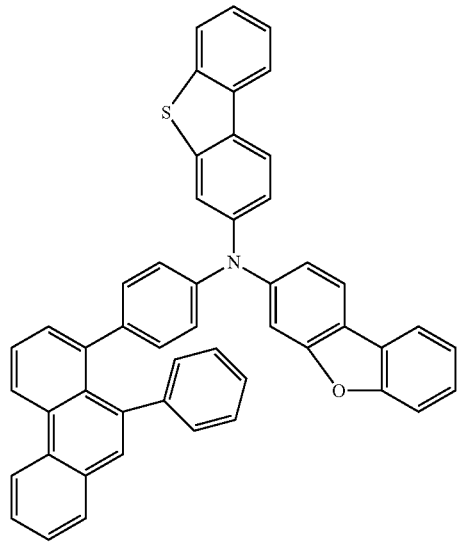
34
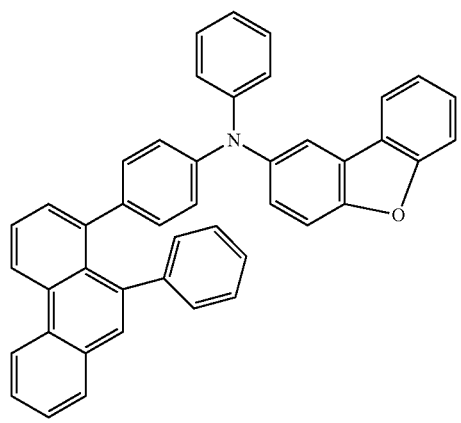

35
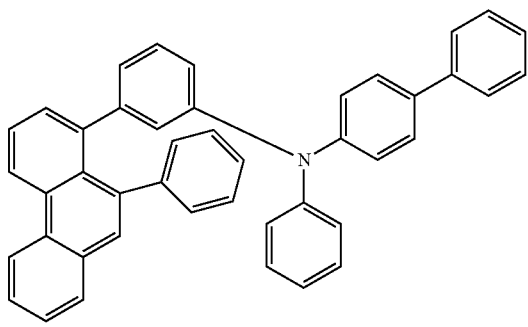
36
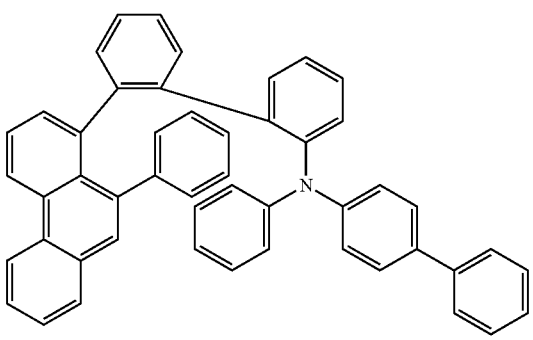
37
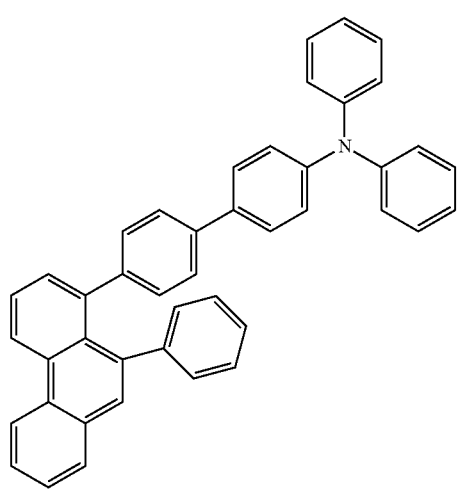
38
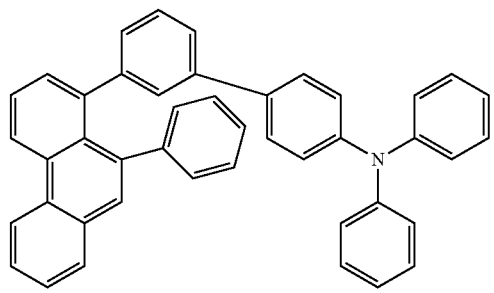
39
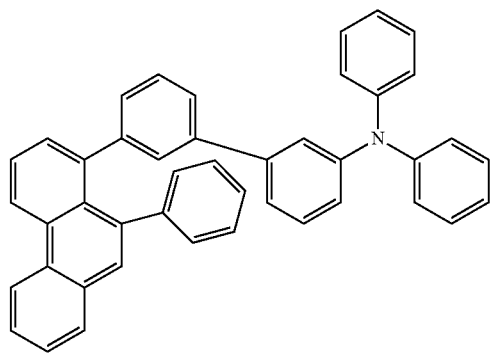
40
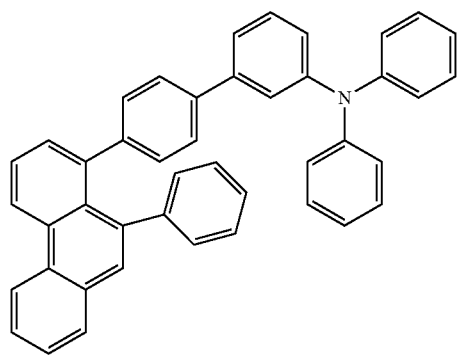

-continued
41
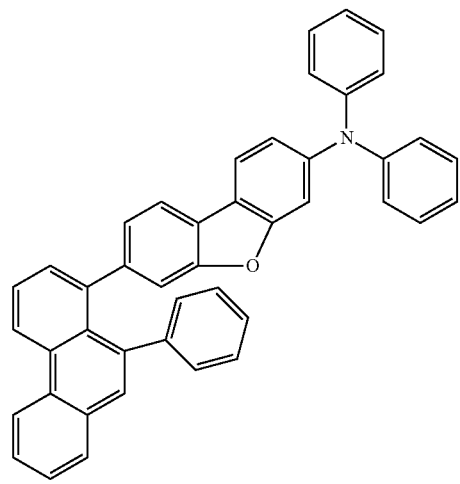
42
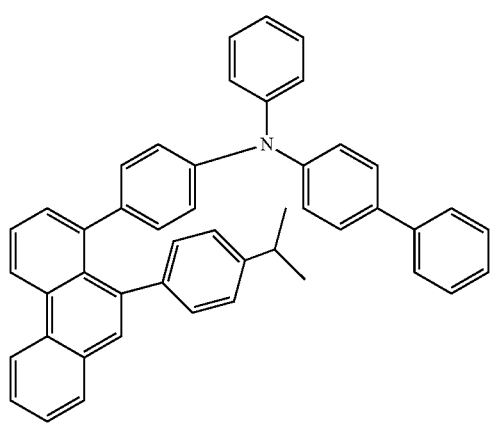
-continued
44
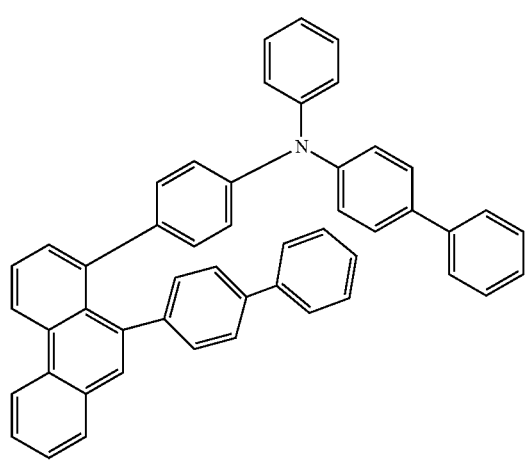
44
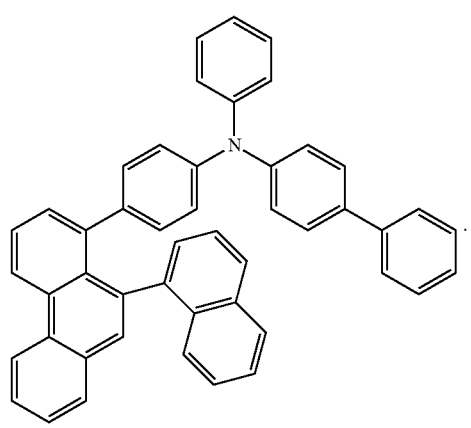
* * * * *

UNITED STATES PATENT AND TRADEMARK OFFICE
CERTIFICATE OF CORRECTION

PATENT NO. : 11,832,512 B2
APPLICATION NO. : 16/565332
DATED : November 28, 2023
INVENTOR(S) : Ichinori Takada It is certified that error appears in the above-identified patent and that said Letters Patent is hereby corrected as shown below:

In the Claims

In Column 58, Line 2, in Claim 11, delete "44" and insert -- 43 --.

In Column 59, Line 32, in Claim 16, delete "Ara" and insert -- $Ar_3$ --.

In Column 74, Line 2, in Claim 20, delete "44" and insert -- 43 --.

Signed and Sealed this
Sixteenth Day of April, 2024

Katherine Kelly Vidal
*Director of the United States Patent and Trademark Office*